United States Patent
Sun et al.

(10) Patent No.: US 12,383,519 B2
(45) Date of Patent: Aug. 12, 2025

(54) APPLICATION OF CaMK4 IN PREPARATION OF MEDICINE FOR PREVENTING AND TREATING PSORIASIS

(71) Applicant: Liangdan Sun, Hefei (CN)

(72) Inventors: Liangdan Sun, Hefei (CN); Liang Yong, Hefei (CN); Qi Zhen, Hefei (CN)

(73) Assignee: Liangdan Sun, Hefei (CN)

( * ) Notice: Subject to any disclaimer, the term of this patent is extended or adjusted under 35 U.S.C. 154(b) by 757 days.

(21) Appl. No.: 17/577,156

(22) Filed: Jan. 17, 2022

(65) Prior Publication Data
US 2022/0226267 A1   Jul. 21, 2022

(30) Foreign Application Priority Data
Jan. 20, 2021   (CN) .......................... 202110075788.2

(51) Int. Cl.
*A61K 31/18*   (2006.01)
*A61P 17/06*   (2006.01)

(52) U.S. Cl.
CPC .............. *A61K 31/18* (2013.01); *A61P 17/06* (2018.01)

(58) Field of Classification Search
CPC .. A61K 31/18; A61P 17/06; C12Y 207/11017
See application file for complete search history.

(56) References Cited

FOREIGN PATENT DOCUMENTS

WO   WO-2011146732 A1 * 11/2011 ............. A61K 31/00

OTHER PUBLICATIONS

Blauvelt et al., Clinical Rev. in Allergy & Immunology, vol. 55, pp. 379-390, publ. Aug. 14, 2018 (Year: 2018).*

* cited by examiner

*Primary Examiner* — Sarah Pihonak
(74) *Attorney, Agent, or Firm* — WPAT, PC

(57) ABSTRACT

An application of CaMK4 as a target in preparation of medicines for preventing and treating psoriasis and an application of a CaMK4 inhibitor in preparation of medicines for preventing and treating psoriasis are provided. The expressions of CaMK4 in skin lesions of patients with psoriasis and IMQ induced skin lesions of mice with psoriasis are detected, and the results show that CaMK4 is positively correlated with psoriasis development. CaMK4 is expressed not only in immune cells, but also in keratinocytes. Moreover, IL-10 and the CaMK4 inhibitor can reduce psoriasiform inflammation induced by IMQ in mice. It shows that CaMK4 can be used as a new target in the preparation of medicines for prevention and treatment of psoriasis.

3 Claims, 24 Drawing Sheets
Specification includes a Sequence Listing.

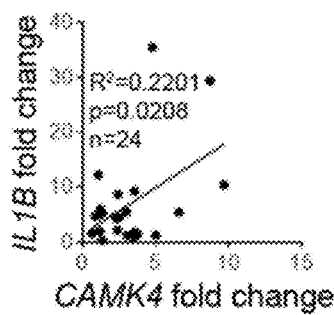 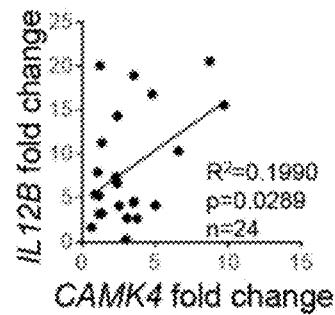
FIG. 4a  FIG. 4b
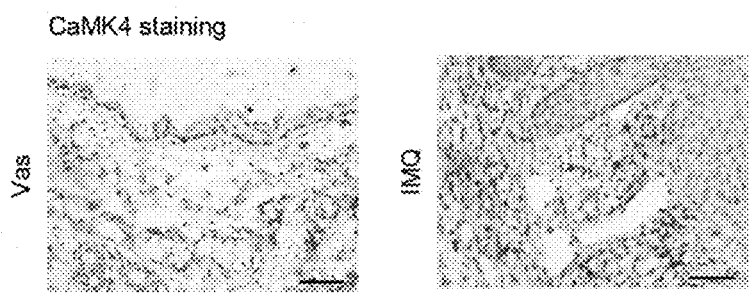
FIG. 5a  FIG. 5b
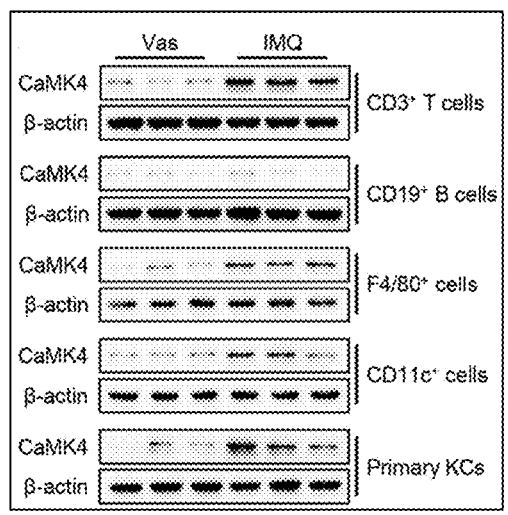
FIG. 6

```
                          SEQUENCE LISTING

<160> NUMBER OF SEQ ID NOS: 100

<210> SEQ ID NO 1
<211> LENGTH: 20
<212> TYPE: DNA
<213> ORGANISM: Artificial Sequence
<220> FEATURE:
<223> OTHER INFORMATION: Gapdh forward primer for mouse

<400> SEQUENCE: 1
gtgttcctac ccccaatgtg                                              20

<210> SEQ ID NO 2
<211> LENGTH: 20
<212> TYPE: DNA
<213> ORGANISM: Artificial Sequence
<220> FEATURE:
<223> OTHER INFORMATION: Gapdh reverse primer for mouse

<400> SEQUENCE: 2
ggtcctcagt gtagcccaag                                              20

<210> SEQ ID NO 3
<211> LENGTH: 21
<212> TYPE: DNA
<213> ORGANISM: Artificial Sequence
<220> FEATURE:
<223> OTHER INFORMATION: Camk4 forward primer for mouse

<400> SEQUENCE: 3
gagaacctcg tcccggatta c                                            21

<210> SEQ ID NO 4
<211> LENGTH: 21
<212> TYPE: DNA
<213> ORGANISM: Artificial Sequence
<220> FEATURE:
<223> OTHER INFORMATION: Camk4 reverse primer for mouse

<400> SEQUENCE: 4
acacaatgga tgtagcaccc c                                            21

<210> SEQ ID NO 5
<211> LENGTH: 22
<212> TYPE: DNA
<213> ORGANISM: Artificial Sequence
<220> FEATURE:
<223> OTHER INFORMATION: S100a8 forward primer for mouse

<400> SEQUENCE: 5
aaatcaccat gccctctaca ag                                           22

<210> SEQ ID NO 6
<211> LENGTH: 22
<212> TYPE: DNA
<213> ORGANISM: Artificial Sequence
<220> FEATURE:
<223> OTHER INFORMATION: S100a8 reverse primer for mouse

<400> SEQUENCE: 6
```

-continued

```
cccactttta tcaccatcgc aa                                              22

<210> SEQ ID NO 7
<211> LENGTH: 20
<212> TYPE: DNA
<213> ORGANISM: Artificial Sequence
<220> FEATURE:
<223> OTHER INFORMATION: S100a9 forward primer for mouse

<400> SEQUENCE: 7
caccctgagc aagaaggaat                                                 20

<210> SEQ ID NO 8
<211> LENGTH: 23
<212> TYPE: DNA
<213> ORGANISM: Artificial Sequence
<220> FEATURE:
<223> OTHER INFORMATION: S100a9  reverse primer for mouse

<400> SEQUENCE: 8
tgtcatttat gagggcttca ttt                                             23

<210> SEQ ID NO 9
<211> LENGTH: 23
<212> TYPE: DNA
<213> ORGANISM: Artificial Sequence
<220> FEATURE:
<223> OTHER INFORMATION: Lcn2 forward primer for mouse

<400> SEQUENCE: 9
acatttgttc caagctccag ggc                                             23

<210> SEQ ID NO 10
<211> LENGTH: 23
<212> TYPE: DNA
<213> ORGANISM: Artificial Sequence
<220> FEATURE:
<223> OTHER INFORMATION: Lcn2 reverse primer for mouse

<400> SEQUENCE: 10
catggcgaac tggttgtagt ccg                                             23

<210> SEQ ID NO 11
<211> LENGTH: 20
<212> TYPE: DNA
<213> ORGANISM: Artificial Sequence
<220> FEATURE:
<223> OTHER INFORMATION: Camp forward primer for mouse

<400> SEQUENCE: 11
gctgtggcgg tcactatcac                                                 20

<210> SEQ ID NO 12
<211> LENGTH: 21
<212> TYPE: DNA
<213> ORGANISM: Artificial Sequence
<220> FEATURE:
<223> OTHER INFORMATION: Camp reverse primer for mouse

<400> SEQUENCE: 12
tgtctaggga ctgctggttg a                                               21

<210> SEQ ID NO 13
<211> LENGTH: 19
<212> TYPE: DNA
<213> ORGANISM: Artificial Sequence
```

```
<220> FEATURE:
<223> OTHER INFORMATION: Tnfa forward primer for mouse

<400> SEQUENCE: 13
actggcagaa gaggcactc                                              19

<210> SEQ ID NO 14
<211> LENGTH: 20
<212> TYPE: DNA
<213> ORGANISM: Artificial Sequence
<220> FEATURE:
<223> OTHER INFORMATION: Tnfa reverse primer for mouse

<400> SEQUENCE: 14
ctggcaccac tagttggttg                                             20

<210> SEQ ID NO 15
<211> LENGTH: 20
<212> TYPE: DNA
<213> ORGANISM: Artificial Sequence
<220> FEATURE:
<223> OTHER INFORMATION: Tgfb1 forward primer for mouse

<400> SEQUENCE: 15
acaattcctg gcgttacctt                                             20

<210> SEQ ID NO 16
<211> LENGTH: 19
<212> TYPE: DNA
<213> ORGANISM: Artificial Sequence
<220> FEATURE:
<223> OTHER INFORMATION: Tgfb1 reverse primer for mouse

<400> SEQUENCE: 16
agccctgtat tccgtctcc                                              19

<210> SEQ ID NO 17
<211> LENGTH: 21
<212> TYPE: DNA
<213> ORGANISM: Artificial Sequence
<220> FEATURE:
<223> OTHER INFORMATION: Ifng forward primer for mouse

<400> SEQUENCE: 17
atgaacgcta cacactgcat c                                           21

<210> SEQ ID NO 18
<211> LENGTH: 20
<212> TYPE: DNA
<213> ORGANISM: Artificial Sequence
<220> FEATURE:
<223> OTHER INFORMATION: Ifng reverse primer for mouse

<400> SEQUENCE: 18
ctggcaccac tagttggttg                                             20

<210> SEQ ID NO 19
<211> LENGTH: 21
<212> TYPE: DNA
<213> ORGANISM: Artificial Sequence
<220> FEATURE:
<223> OTHER INFORMATION: Il1b forward primer for mouse

<400> SEQUENCE: 19
ctgaactcaa ctgtgaaatg c                                           21
```

<210> SEQ ID NO 20
<211> LENGTH: 18
<212> TYPE: DNA
<213> ORGANISM: Artificial Sequence
<220> FEATURE:
<223> OTHER INFORMATION: Il1b reverse primer for mouse

<400> SEQUENCE: 20
tgatgtgctg ctgcgaga                                                 18

<210> SEQ ID NO 21
<211> LENGTH: 21
<212> TYPE: DNA
<213> ORGANISM: Artificial Sequence
<220> FEATURE:
<223> OTHER INFORMATION: Il10 forward primer for mouse

<400> SEQUENCE: 21
gctcttactg actggcatga g                                             21

<210> SEQ ID NO 22
<211> LENGTH: 20
<212> TYPE: DNA
<213> ORGANISM: Artificial Sequence
<220> FEATURE:
<223> OTHER INFORMATION: Il10 reverse primer for mouse

<400> SEQUENCE: 22
cgcagctcta ggagcatgtg                                               20

<210> SEQ ID NO 23
<211> LENGTH: 21
<212> TYPE: DNA
<213> ORGANISM: Artificial Sequence
<220> FEATURE:
<223> OTHER INFORMATION: Il17a forward primer for mouse

<400> SEQUENCE: 23
tttaactccc ttggcgcaaa a                                             21

<210> SEQ ID NO 24
<211> LENGTH: 20
<212> TYPE: DNA
<213> ORGANISM: Artificial Sequence
<220> FEATURE:
<223> OTHER INFORMATION: Il17a reverse primer for mouse

<400> SEQUENCE: 24
ctttccctcc gcattgacac                                               20

<210> SEQ ID NO 25
<211> LENGTH: 22
<212> TYPE: DNA
<213> ORGANISM: Artificial Sequence
<220> FEATURE:
<223> OTHER INFORMATION: Il17f forward primer for mouse

<400> SEQUENCE: 25
aaccagggca tttctgtccc ac                                            22

<210> SEQ ID NO 26
<211> LENGTH: 22
<212> TYPE: DNA
<213> ORGANISM: Artificial Sequence
<220> FEATURE:
<223> OTHER INFORMATION: Il17f reverse primer for mouse

```
<400> SEQUENCE: 26
ggcattgatg cagcctgagt gt                                        22

<210> SEQ ID NO 27
<211> LENGTH: 23
<212> TYPE: DNA
<213> ORGANISM: Artificial Sequence
<220> FEATURE:
<223> OTHER INFORMATION: Il22 forward primer for mouse

<400> SEQUENCE: 27
atgagttttt cccttatggg gac                                       23

<210> SEQ ID NO 28
<211> LENGTH: 21
<212> TYPE: DNA
<213> ORGANISM: Artificial Sequence
<220> FEATURE:
<223> OTHER INFORMATION: Il22 reverse primer for mouse

<400> SEQUENCE: 28
gctggaagtt ggacacctca a                                         21

<210> SEQ ID NO 29
<211> LENGTH: 21
<212> TYPE: DNA
<213> ORGANISM: Artificial Sequence
<220> FEATURE:
<223> OTHER INFORMATION: Il23a forward primer for mouse

<400> SEQUENCE: 29
atgctggatt gcagagcagt a                                         21

<210> SEQ ID NO 30
<211> LENGTH: 23
<212> TYPE: DNA
<213> ORGANISM: Artificial Sequence
<220> FEATURE:
<223> OTHER INFORMATION: Il23a reverse primer for mouse

<400> SEQUENCE: 30
acggggcaca ttattttag tct                                        23

<210> SEQ ID NO 31
<211> LENGTH: 20
<212> TYPE: DNA
<213> ORGANISM: Artificial Sequence
<220> FEATURE:
<223> OTHER INFORMATION: Ccl2 forward primer for mouse

<400> SEQUENCE: 31
ccagcaagat gatcccaatg                                           20

<210> SEQ ID NO 32
<211> LENGTH: 20
<212> TYPE: DNA
<213> ORGANISM: Artificial Sequence
<220> FEATURE:
<223> OTHER INFORMATION: Ccl2 reverse primer for mouse

<400> SEQUENCE: 32
tacgggtcaa cttcacattc                                           20

<210> SEQ ID NO 33
```

```
<211> LENGTH: 20
<212> TYPE: DNA
<213> ORGANISM: Artificial Sequence
<220> FEATURE:
<223> OTHER INFORMATION: Ccl20 forward primer for mouse

<400> SEQUENCE: 33
aatctgtgtg cgctgatcca                                              20

<210> SEQ ID NO 34
<211> LENGTH: 20
<212> TYPE: DNA
<213> ORGANISM: Artificial Sequence
<220> FEATURE:
<223> OTHER INFORMATION: Ccl20 reverse primer for mouse

<400> SEQUENCE: 34
ccttgggctg tgtccaattc                                              20

<210> SEQ ID NO 35
<211> LENGTH: 20
<212> TYPE: DNA
<213> ORGANISM: Artificial Sequence
<220> FEATURE:
<223> OTHER INFORMATION: Cd36 forward primer for mouse

<400> SEQUENCE: 35
atgggctgtg atcggaactg                                              20

<210> SEQ ID NO 36
<211> LENGTH: 21
<212> TYPE: DNA
<213> ORGANISM: Artificial Sequence
<220> FEATURE:
<223> OTHER INFORMATION: Cd36 reverse primer for mouse

<400> SEQUENCE: 36
tttgccacgt catctgggtt t                                            21

<210> SEQ ID NO 37
<211> LENGTH: 21
<212> TYPE: DNA
<213> ORGANISM: Artificial Sequence
<220> FEATURE:
<223> OTHER INFORMATION: Macro forward primer for mouse

<400> SEQUENCE: 37
acagagccga ttttgaccaa g                                            21

<210> SEQ ID NO 38
<211> LENGTH: 19
<212> TYPE: DNA
<213> ORGANISM: Artificial Sequence
<220> FEATURE:
<223> OTHER INFORMATION: Macro reverse primer for mouse

<400> SEQUENCE: 38
cagcagtgca gtacctgcc                                               19

<210> SEQ ID NO 39
<211> LENGTH: 21
<212> TYPE: DNA
<213> ORGANISM: Artificial Sequence
<220> FEATURE:
<223> OTHER INFORMATION: Trem2 forward primer for mouse

<400> SEQUENCE: 39
```

-continued

```
ctggaaccgt caccatcact c                                              21

<210> SEQ ID NO 40
<211> LENGTH: 21
<212> TYPE: DNA
<213> ORGANISM: Artificial Sequence
<220> FEATURE:
<223> OTHER INFORMATION: Trem2 reverse primer for mouse

<400> SEQUENCE: 40
cgaaactcga tgactcctcg g                                              21

<210> SEQ ID NO 41
<211> LENGTH: 19
<212> TYPE: DNA
<213> ORGANISM: Artificial Sequence
<220> FEATURE:
<223> OTHER INFORMATION: Axl forward primer for mouse

<400> SEQUENCE: 41
atggccgaca ttgccagtg                                                 19

<210> SEQ ID NO 42
<211> LENGTH: 22
<212> TYPE: DNA
<213> ORGANISM: Artificial Sequence
<220> FEATURE:
<223> OTHER INFORMATION: Axl reverse primer for mouse

<400> SEQUENCE: 42
cggtagtaat ccccgttgta ga                                             22

<210> SEQ ID NO 43
<211> LENGTH: 20
<212> TYPE: DNA
<213> ORGANISM: Artificial Sequence
<220> FEATURE:
<223> OTHER INFORMATION: Mertk forward primer for mouse

<400> SEQUENCE: 43
cagggccttt accagggaga                                                20

<210> SEQ ID NO 44
<211> LENGTH: 21
<212> TYPE: DNA
<213> ORGANISM: Artificial Sequence
<220> FEATURE:
<223> OTHER INFORMATION: Mertk reverse primer for mouse

<400> SEQUENCE: 44
tgtgtgctgg atgtgatctt c                                              21

<210> SEQ ID NO 45
<211> LENGTH: 22
<212> TYPE: DNA
<213> ORGANISM: Artificial Sequence
<220> FEATURE:
<223> OTHER INFORMATION: Gpnmb forward primer for mouse

<400> SEQUENCE: 45
cattcccatc tcgaaggtga aa                                             22

<210> SEQ ID NO 46
<211> LENGTH: 21
<212> TYPE: DNA
```

```
<213> ORGANISM: Artificial Sequence
<220> FEATURE:
<223> OTHER INFORMATION: Gpnmb reverse primer for mouse

<400> SEQUENCE: 46
aaatggcaga gtcgttgagg a                                           21

<210> SEQ ID NO 47
<211> LENGTH: 19
<212> TYPE: DNA
<213> ORGANISM: Artificial Sequence
<220> FEATURE:
<223> OTHER INFORMATION: Cd81 forward primer for mouse

<400> SEQUENCE: 47
gtggagggct gcaccaaat                                              19

<210> SEQ ID NO 48
<211> LENGTH: 20
<212> TYPE: DNA
<213> ORGANISM: Artificial Sequence
<220> FEATURE:
<223> OTHER INFORMATION: Cd81 reverse primer for mouse

<400> SEQUENCE: 48
gacgcaacca cagagctaca                                             20

<210> SEQ ID NO 49
<211> LENGTH: 23
<212> TYPE: DNA
<213> ORGANISM: Artificial Sequence
<220> FEATURE:
<223> OTHER INFORMATION: Cd5l forward primer for mouse

<400> SEQUENCE: 49
gatcgtgttt ttcagagtct cca                                         23

<210> SEQ ID NO 50
<211> LENGTH: 22
<212> TYPE: DNA
<213> ORGANISM: Artificial Sequence
<220> FEATURE:
<223> OTHER INFORMATION: Cd5l reverse primer for mouse

<400> SEQUENCE: 50
tgcagtcaac cccttgaata ag                                          22

<210> SEQ ID NO 51
<211> LENGTH: 23
<212> TYPE: DNA
<213> ORGANISM: Artificial Sequence
<220> FEATURE:
<223> OTHER INFORMATION: Fcrls forward primer for mouse

<400> SEQUENCE: 51
acaggatcta agtggctgaa tgt                                         23

<210> SEQ ID NO 52
<211> LENGTH: 20
<212> TYPE: DNA
<213> ORGANISM: Artificial Sequence
<220> FEATURE:
<223> OTHER INFORMATION: Fcrls reverse primer for mouse

<400> SEQUENCE: 52
ctgggtcgtt gccctatctg                                             20
```

```
<210> SEQ ID NO 53
<211> LENGTH: 21
<212> TYPE: DNA
<213> ORGANISM: Artificial Sequence
<220> FEATURE:
<223> OTHER INFORMATION: Cd80 forward primer for mouse

<400> SEQUENCE: 53
acccccaaca taactgagtc t                                              21

<210> SEQ ID NO 54
<211> LENGTH: 21
<212> TYPE: DNA
<213> ORGANISM: Artificial Sequence
<220> FEATURE:
<223> OTHER INFORMATION: Cd80 reverse primer for mouse

<400> SEQUENCE: 54
ttccaaccaa gagaagcgag g                                              21

<210> SEQ ID NO 55
<211> LENGTH: 20
<212> TYPE: DNA
<213> ORGANISM: Artificial Sequence
<220> FEATURE:
<223> OTHER INFORMATION: Cd86 forward primer for mouse

<400> SEQUENCE: 55
tgtttccgtg gagacgcaag                                                20

<210> SEQ ID NO 56
<211> LENGTH: 21
<212> TYPE: DNA
<213> ORGANISM: Artificial Sequence
<220> FEATURE:
<223> OTHER INFORMATION: Cd86 reverse primer for mouse

<400> SEQUENCE: 56
ttgagccttt gtaaatgggc a                                              21

<210> SEQ ID NO 57
<211> LENGTH: 23
<212> TYPE: DNA
<213> ORGANISM: Artificial Sequence
<220> FEATURE:
<223> OTHER INFORMATION: Nos2 forward primer for mouse

<400> SEQUENCE: 57
gttctcagcc caacaataca aga                                            23

<210> SEQ ID NO 58
<211> LENGTH: 19
<212> TYPE: DNA
<213> ORGANISM: Artificial Sequence
<220> FEATURE:
<223> OTHER INFORMATION: Nos2 reverse primer for mouse

<400> SEQUENCE: 58
gtggacgggt cgatgtcac                                                 19

<210> SEQ ID NO 59
<211> LENGTH: 21
<212> TYPE: DNA
<213> ORGANISM: Artificial Sequence
<220> FEATURE:
```

```
<223> OTHER INFORMATION: Arg1 forward primer for mouse

<400> SEQUENCE: 59
aacacggcag tggctttaac c                                         21

<210> SEQ ID NO 60
<211> LENGTH: 20
<212> TYPE: DNA
<213> ORGANISM: Artificial Sequence
<220> FEATURE:
<223> OTHER INFORMATION: Arg1 reverse primer for mouse

<400> SEQUENCE: 60
ggttttcatg tggcgcattc                                           20

<210> SEQ ID NO 61
<211> LENGTH: 23
<212> TYPE: DNA
<213> ORGANISM: Artificial Sequence
<220> FEATURE:
<223> OTHER INFORMATION: Retnla forward primer for mouse

<400> SEQUENCE: 61
ccaatccagc taactatccc tcc                                       23

<210> SEQ ID NO 62
<211> LENGTH: 21
<212> TYPE: DNA
<213> ORGANISM: Artificial Sequence
<220> FEATURE:
<223> OTHER INFORMATION: Retnla reverse primer for mouse

<400> SEQUENCE: 62
ccagtcaacg agtaagcaca g                                         21

<210> SEQ ID NO 63
<211> LENGTH: 23
<212> TYPE: DNA
<213> ORGANISM: Artificial Sequence
<220> FEATURE:
<223> OTHER INFORMATION: Chil3 forward primer for mouse

<400> SEQUENCE: 63
tctgaaagac aagaacactg agc                                       23

<210> SEQ ID NO 64
<211> LENGTH: 20
<212> TYPE: DNA
<213> ORGANISM: Artificial Sequence
<220> FEATURE:
<223> OTHER INFORMATION: Chil3 reverse primer for mouse

<400> SEQUENCE: 64
gcaggtccaa acttccatcc                                           20

<210> SEQ ID NO 65
<211> LENGTH: 22
<212> TYPE: DNA
<213> ORGANISM: Artificial Sequence
<220> FEATURE:
<223> OTHER INFORMATION: GAPDH forward primer for human

<400> SEQUENCE: 65
gtctcctctg acttcaacag cg                                        22
```

```
<210> SEQ ID NO 66
<211> LENGTH: 22
<212> TYPE: DNA
<213> ORGANISM: Artificial Sequence
<220> FEATURE:
<223> OTHER INFORMATION: GAPDH reverse primer for human

<400> SEQUENCE: 66
accaccctgt tgctgtagcc aa                                              22

<210> SEQ ID NO 67
<211> LENGTH: 23
<212> TYPE: DNA
<213> ORGANISM: Artificial Sequence
<220> FEATURE:
<223> OTHER INFORMATION: CAMK4 forward primer for human

<400> SEQUENCE: 67
gttcttcttc gcctctcaca tcc                                             23

<210> SEQ ID NO 68
<211> LENGTH: 22
<212> TYPE: DNA
<213> ORGANISM: Artificial Sequence
<220> FEATURE:
<223> OTHER INFORMATION: CAMK4 reverse primer for human

<400> SEQUENCE: 68
ctgtgacgag ttctaggacc ag                                              22

<210> SEQ ID NO 69
<211> LENGTH: 22
<212> TYPE: DNA
<213> ORGANISM: Artificial Sequence
<220> FEATURE:
<223> OTHER INFORMATION: S100A8 forward primer for human

<400> SEQUENCE: 69
atgccgtcta cagggatgac ct                                              22

<210> SEQ ID NO 70
<211> LENGTH: 24
<212> TYPE: DNA
<213> ORGANISM: Artificial Sequence
<220> FEATURE:
<223> OTHER INFORMATION: S100A8 reverse primer for human

<400> SEQUENCE: 70
agaatgagga actcctggaa gtta                                            24

<210> SEQ ID NO 71
<211> LENGTH: 21
<212> TYPE: DNA
<213> ORGANISM: Artificial Sequence
<220> FEATURE:
<223> OTHER INFORMATION: S100A9 forward primer for human

<400> SEQUENCE: 71
gcacccagac accctgaacc a                                               21

<210> SEQ ID NO 72
<211> LENGTH: 22
<212> TYPE: DNA
<213> ORGANISM: Artificial Sequence
<220> FEATURE:
<223> OTHER INFORMATION: S100A9 reverse primer for human
```

```
<400> SEQUENCE: 72
tgtgtccagg tcctccatga tg                                          22

<210> SEQ ID NO 73
<211> LENGTH: 22
<212> TYPE: DNA
<213> ORGANISM: Artificial Sequence
<220> FEATURE:
<223> OTHER INFORMATION: CAMP forward primer for human

<400> SEQUENCE: 73
gacacagcag tcaccagagg at                                          22

<210> SEQ ID NO 74
<211> LENGTH: 23
<212> TYPE: DNA
<213> ORGANISM: Artificial Sequence
<220> FEATURE:
<223> OTHER INFORMATION: CAMP reverse primer for human

<400> SEQUENCE: 74
tcacaactga tgtcaaagga gcc                                         23

<210> SEQ ID NO 75
<211> LENGTH: 20
<212> TYPE: DNA
<213> ORGANISM: Artificial Sequence
<220> FEATURE:
<223> OTHER INFORMATION: DEFB4A forward primer for human

<400> SEQUENCE: 75
gttccacagc tccaccttca                                             20

<210> SEQ ID NO 76
<211> LENGTH: 20
<212> TYPE: DNA
<213> ORGANISM: Artificial Sequence
<220> FEATURE:
<223> OTHER INFORMATION: DEFB4A reverse primer for human

<400> SEQUENCE: 76
cacagcccag gacttccttt                                             20

<210> SEQ ID NO 77
<211> LENGTH: 20
<212> TYPE: DNA
<213> ORGANISM: Artificial Sequence
<220> FEATURE:
<223> OTHER INFORMATION: SPRR2A forward primer for human

<400> SEQUENCE: 77
gttccacagc tccaccttca                                             20

<210> SEQ ID NO 78
<211> LENGTH: 20
<212> TYPE: DNA
<213> ORGANISM: Artificial Sequence
<220> FEATURE:
<223> OTHER INFORMATION: SPRR2A reverse primer for human

<400> SEQUENCE: 78
cacagcccag gacttccttt                                             20

<210> SEQ ID NO 79
<211> LENGTH: 24
```

```
<212> TYPE: DNA
<213> ORGANISM: Artificial Sequence
<220> FEATURE:
<223> OTHER INFORMATION: SPRR2B forward primer for human

<400> SEQUENCE: 79
actggttaat cctgagactc cagc                                          24

<210> SEQ ID NO 80
<211> LENGTH: 22
<212> TYPE: DNA
<213> ORGANISM: Artificial Sequence
<220> FEATURE:
<223> OTHER INFORMATION: SPRR2B reverse primer for human

<400> SEQUENCE: 80
aggaggatat ttctgctggc ac                                            22

<210> SEQ ID NO 81
<211> LENGTH: 22
<212> TYPE: DNA
<213> ORGANISM: Artificial Sequence
<220> FEATURE:
<223> OTHER INFORMATION: IL1B forward primer for human

<400> SEQUENCE: 81
ccacagacct tccaggagaa tg                                            22

<210> SEQ ID NO 82
<211> LENGTH: 23
<212> TYPE: DNA
<213> ORGANISM: Artificial Sequence
<220> FEATURE:
<223> OTHER INFORMATION: IL1B reverse primer for human

<400> SEQUENCE: 82
gtgcagttca gtgatcgtac agg                                           23

<210> SEQ ID NO 83
<211> LENGTH: 24
<212> TYPE: DNA
<213> ORGANISM: Artificial Sequence
<220> FEATURE:
<223> OTHER INFORMATION: IL6 forward primer for human

<400> SEQUENCE: 83
aaattcggta catcctcgac ggca                                          24

<210> SEQ ID NO 84
<211> LENGTH: 24
<212> TYPE: DNA
<213> ORGANISM: Artificial Sequence
<220> FEATURE:
<223> OTHER INFORMATION: IL6 reverse primer for human

<400> SEQUENCE: 84
agtgcctctt tgctgctttc acac                                          24

<210> SEQ ID NO 85
<211> LENGTH: 23
<212> TYPE: DNA
<213> ORGANISM: Artificial Sequence
<220> FEATURE:
<223> OTHER INFORMATION: IL10 forward primer for human

<400> SEQUENCE: 85
```

```
gactttaagg gttacctggg ttg                                        23

<210> SEQ ID NO 86
<211> LENGTH: 21
<212> TYPE: DNA
<213> ORGANISM: Artificial Sequence
<220> FEATURE:
<223> OTHER INFORMATION: IL10 reverse primer for human

<400> SEQUENCE: 86
tcacatgcgc cttgatgtct g                                          21

<210> SEQ ID NO 87
<211> LENGTH: 22
<212> TYPE: DNA
<213> ORGANISM: Artificial Sequence
<220> FEATURE:
<223> OTHER INFORMATION: IL12B forward primer for human

<400> SEQUENCE: 87
gacattctgc gttcaggtcc ag                                         22

<210> SEQ ID NO 88
<211> LENGTH: 23
<212> TYPE: DNA
<213> ORGANISM: Artificial Sequence
<220> FEATURE:
<223> OTHER INFORMATION: IL12B reverse primer for human

<400> SEQUENCE: 88
catttttgcg gcagatgacc gtg                                        23

<210> SEQ ID NO 89
<211> LENGTH: 23
<212> TYPE: DNA
<213> ORGANISM: Artificial Sequence
<220> FEATURE:
<223> OTHER INFORMATION: IL17A forward primer for human

<400> SEQUENCE: 89
agattactac aaccgatcca cct                                        23

<210> SEQ ID NO 90
<211> LENGTH: 21
<212> TYPE: DNA
<213> ORGANISM: Artificial Sequence
<220> FEATURE:
<223> OTHER INFORMATION: IL17A reverse primer for human

<400> SEQUENCE: 90
ggggacagag ttcatgtggt a                                          21

<210> SEQ ID NO 91
<211> LENGTH: 22
<212> TYPE: DNA
<213> ORGANISM: Artificial Sequence
<220> FEATURE:
<223> OTHER INFORMATION: IL23A forward primer for human

<400> SEQUENCE: 91
gagccttctc tgctccctga ta                                         22

<210> SEQ ID NO 92
<211> LENGTH: 22
<212> TYPE: DNA
<213> ORGANISM: Artificial Sequence
```

```
<220> FEATURE:
<223> OTHER INFORMATION: IL23A reverse primer for human

<400> SEQUENCE: 92
gactgaggct tggaatctgc tg                                              22

<210> SEQ ID NO 93
<211> LENGTH: 22
<212> TYPE: DNA
<213> ORGANISM: Artificial Sequence
<220> FEATURE:
<223> OTHER INFORMATION: TNFA forward primer for human

<400> SEQUENCE: 93
ctcttctgcc tgctgcactt tg                                              22

<210> SEQ ID NO 94
<211> LENGTH: 22
<212> TYPE: DNA
<213> ORGANISM: Artificial Sequence
<220> FEATURE:
<223> OTHER INFORMATION: TNFA reverse primer for human

<400> SEQUENCE: 94
atgggctaca ggcttgtcac tc                                              22

<210> SEQ ID NO 95
<211> LENGTH: 21
<212> TYPE: DNA
<213> ORGANISM: Artificial Sequence
<220> FEATURE:
<223> OTHER INFORMATION: TGFB1 forward primer for human

<400> SEQUENCE: 95
caattcctgg cgatacctca g                                               21

<210> SEQ ID NO 96
<211> LENGTH: 21
<212> TYPE: DNA
<213> ORGANISM: Artificial Sequence
<220> FEATURE:
<223> OTHER INFORMATION: TGFB1 reverse primer for human

<400> SEQUENCE: 96
gcacaactcc ggtgacatca a                                               21

<210> SEQ ID NO 97
<211> LENGTH: 23
<212> TYPE: DNA
<213> ORGANISM: Artificial Sequence
<220> FEATURE:
<223> OTHER INFORMATION: CCL2 forward primer for human

<400> SEQUENCE: 97
agaatcacca gcagcaagtg tcc                                             23

<210> SEQ ID NO 98
<211> LENGTH: 22
<212> TYPE: DNA
<213> ORGANISM: Artificial Sequence
<220> FEATURE:
<223> OTHER INFORMATION: CCL2 reverse primer for human

<400> SEQUENCE: 98
tcctgaaccc acttctgctt gg                                              22
```

```
<210> SEQ ID NO 99
<211> LENGTH: 23
<212> TYPE: DNA
<213> ORGANISM: Artificial Sequence
<220> FEATURE:
<223> OTHER INFORMATION: CCL20 forward primer for human

<400> SEQUENCE: 99
aagttgtctg tgtgcgcaaa tcc                                              23

<210> SEQ ID NO 100
<211> LENGTH: 24
<212> TYPE: DNA
<213> ORGANISM: Artificial Sequence
<220> FEATURE:
<223> OTHER INFORMATION: CCL20 reverse primer for human

<400> SEQUENCE: 100
ccattccaga aaagccacag tttt                                             24
```

APPLICATION OF CaMK4 IN PREPARATION OF MEDICINE FOR PREVENTING AND TREATING PSORIASIS

TECHNICAL FIELD

The invention relates to the field of biomedical technologies, in particular, to an application/use of CaMK4 in preparation of a medicine for preventing and treating psoriasis.

BACKGROUND

Psoriasis is a chronic inflammatory immune skin disease that manifests clinically as red papules and plaques covered with thick silver-white scaling. A large number of immune cells, such as T-lymphocytes (also referred to as T cells), macrophages, dendritic cells and keratinocytes, play an important role. When being activated, immune cells will release cytokines to stimulate the keratinocytes, resulting in abnormal proliferation of the keratinocytes and formation of dermatokeratinization and scaling.

Calcium/calmodulin-dependent protein kinase IV encoded by CaMK4 gene, is expressed in a variety of cells, especially in T cells. CaMK4 mainly plays an important role in immune response, including activation and development of the T cells, and regulates gene expression by activating transcription factors adenosine cyclophosphate-response element binding protein (CREB), adenosine cyclophosphate-response element modulator alpha CREMα), and retinoic acid receptor-related orphan nuclear receptor gamma t (ROR γt) in immune cells (including T cells and antigen-presenting cells).

At present, the research of CaMK4 gene dysfunction mainly focuses on systemic lupus erythematosus and lupus nephritis, which leads to autoantibody production, immune complex formation and immune disorder, especially closely related to helper T 17 (Th17) cells. It has been reported that CaMK4 regulates differentiation of Th17 cells and expression of interleukin-17A (IL-17A) through protein kinase B (AKT)/mammalian target of rapamycin (mTOR)/S6K/ROR γt and CREM/ROR γt pathways, indicating that CaMK4 is an important signal molecule for the differentiation of nave CD4$^+$ T cells into Th17 cells.

CaMK4 can affect the differentiation of Th17 cells and the production of IL-17A, which not only indicates that CaMK4 is an important and necessary link in the differentiation and action of Th17 cells, but also indicates that CaMK4 may become a new therapeutic target for autoimmune inflammatory diseases. Because immune cells dominated by Th17 cells are involved in the occurrence and development of many autoimmune diseases, it is speculated that CaMK4 may play an important role in the pathogenesis of psoriasis and may become a new therapeutic target for psoriasis.

SUMMARY

The purpose of the invention is to provide an application of CaMK4 in preparation of a medicine for preventing and treating psoriasis, so as to solve the problems existing in the above prior art, and take CaMK4 as a medicine target to realize the effective prevention and treatment of psoriasis.

In order to achieve the above purpose, the invention provides the following solutions:

In an aspect, the invention provides an application of CaMK4 as a target in preparation of a medicine for preventing and treating psoriasis.

In an embodiment, the medicine takes CaMK4 as a medicine target at a genetic level and/or a protein level.

In an embodiment, the medicine is a medicine hindering a protein expression or a mRNA expression of CaMK4.

In an embodiment, the medicine is a medicine blocking a recovery of IL-10 caused by CaMK4.

In another aspect, the invention also provides an application of a CaMK4 inhibitor in preparation of a medicine for preventing and treating psoriasis.

In an embodiment, the CaMK4 inhibitor is used to prevent psoriasis through blocking a protein expression or a mRNA expression of CaMK4.

The invention discloses the following technical effects:

The invention used immunohistochemistry, real-time quantitative polymerase chain reaction (PCR), and Western blot to analyze the expression of CaMK4 in psoriasis patients' skin lesions and imiquimod (IMQ)-induced psoriasis skin lesions in mice, and the results show that CaMK4 is positively correlated with the development of psoriasis. A CaMK4-deficient (CaMK4$^{-/-}$) mouse psoriasis model is constructed by IMQ induction, compared with wild-type (CaMK4$^{+/+}$) mice, which can significantly reduce skin thickness, scaling and epidermal thickness. Moreover, in vivo experiments in mice, through bone marrow-derived macrophages (BMDM) transfusion, exogenous administration of IL-10 and CaMK4 inhibitor KN-93, it was found that inhibiting the expression of CaMK4 in immune cells or keratinocytes can reduce skin thickness, scaling, epidermal thickness and expression of proinflammatory cytokines. In addition, the psoriasiform phenotype in mice with IMQ induced macrophage specific knockout CaMK4 (CaMK4$^{fl/fl}$ Lyz2 Cre) was less than that of control (CaMK4$^{fl/fl}$) mice. Therefore, the invention proposes a new action target CaMK4 when preparing the medicine for preventing and treating psoriasis.

BRIEF DESCRIPTION OF DRAWINGS

FIGS. 4a-4b show correlation between proinflammatory gene in peripheral blood and CaMK4 expression in psoriasis patients.

FIGS. 5a-5b show expression detected by immunohistochemistry of CaMK4 in skin of a mouse model (scale bar: 50 μm).

FIG. 6 shows protein levels of CaMK4 detected by Western blot in mouse keratinocytes (KCs) and CD3$^+$ T cells, CD19$^+$ B cells, F4/80$^+$ cells and CD11c$^+$ cells of mouse skin sorted by magnetic beads.

DETAILED DESCRIPTION OF EMBODIMENTS

Figures 1A, 1B, 1C, 1D:
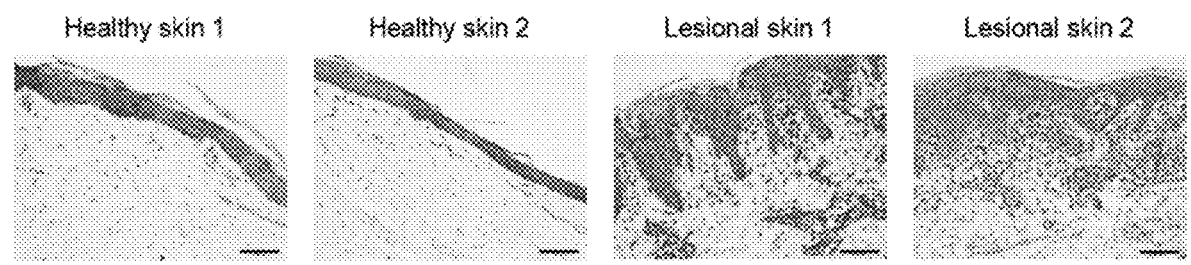
FIGS. 1a-1d show expressions of CaMK4 detected by immunohistochemistry in healthy skin and psoriasis patient's lesional skin (scale bar: 100 μm).

Various exemplary examples of the invention are described in detail. The detailed description should not be considered as a limitation of the invention, but should be understood as a more detailed description of some aspects, characteristics and examples of the invention.

It should be understood that the terms described in the invention are only for describing special examples and are not used to limit the invention. In addition, for the numerical range in the invention, it should be understood that each intermediate value between the upper and lower limits of the range is also specifically disclosed. Each smaller range between any stated value or intermediate value within the stated range and any other stated value or intermediate value within the range are also included in the invention. The upper and lower limits of these smaller ranges can be independently included or excluded from the range.

Unless otherwise stated, all technical and scientific terms used herein have the same meanings generally understood by those skilled in the related art of the invention. Although the invention only describes preferred methods and materials, any method and material similar or equivalent to that described herein may also be used in the implementation or testing of the invention. All documents mentioned in this specification are incorporated by reference to disclose and describe methods and/or materials related to the documents. In case of conflict with any incorporated literature, the contents of this specification shall prevail.

It will be apparent to those skilled in the related art that various improvements and changes can be made to the specific examples of the description of the invention without departing from the scope or spirit of the invention. Other examples obtained from the description of the invention will be apparent to those skilled in the related art. The description and examples of the invention are only exemplary.

The terms "contain", "include", "have", "with" etc. used in this document are open-ended terms, i.e., meaning including but not limited to.

The reagents or materials used in the following examples are commercially available if not otherwise specified.

The invention finds that CaMK4 is significantly increased in skin lesions of psoriasis patients and imiquimod (IMQ)-induced psoriasis skin lesions in mice, suggesting that CaMK4 is positively correlated with psoriasis development, which will be further explained with specific examples below.

EXAMPLE 1

Experimental Materials and Methods

1) Skin Lesion Samples from Patients with Psoriasis

Patients with typical clinical manifestations of psoriasis (33 cases) were selected from the outpatients of the Department of Dermatology of the First Affiliated Hospital of Anhui Medical University, China, of which 9 cases were taken from lesion sites and normal skin samples at the edges of the lesions in saline by conventional methods, and the samples were processed on the same day to prepare pathological sections; 24 cases were taken from blood by conventional methods, mixed 1:3 with Trizol and then lyophilized at −80° C. for RNA extraction.

2) Establishment of a Mouse Model of Psoriasis

An internationally used mouse model of psoriasis was used: 6-8-week-old C57BL/6 mice were given 5% IMQ applied to the shaved back skin of the mice at 62.5 mg per day for 5 days. The 6-8-week-old C57BL/6 mice were used as controls.

3) RNA Extraction and Real-Time Quantitative PCR

The total RNA of tissues or cells was extracted by Tritzol. Specifically, 1 milliliter (ml) Trizol was added to tissues or cells, the tissues were homogenized with homogenizer, and the cells were fully lysed by repeated blowing; then 200 microliters (nL) chloroform were added, vortexed shaken for 15 seconds (s), and stood at room temperature for 10 min, thereby obtaining a first mixed solution. The first mixed solution was centrifuged at 12000 g (g is the gravitational acceleration) for 15 min at 4° C., and the supernatant of the first mixed solution was carefully aspirated about 500 μL in an eppendorf (EP) tube, then an equal volume of isopropanol precooled at 4° C. was added, gently inverted and mixed, and left to stand for 10 min at room temperature, thereby obtaining a second mixed solution. The second mixed solution was centrifuged at 12000 g for 15 min at 4° C. and the supernatant was discarded, 1 ml of 75% ethanol was added and washed twice, 20 μL of DEPC-treated water were added after dried, and the concentration and purity were determined by Nanodrop2000 for use.

A reverse transcription Kit (TaKaRa) was applied to synthesize the complementary DNA (cDNA) of each sample, and then the cDNA was used as a template to amplify the gene fragment. The relative expression of target gene was calculated using 2-ΔΔCt.

All amplification primers used in the invention are as follows:

| Gene | Forward primer(5'-3') | Reverse primer(5'-3') |
|---|---|---|
| Mouse primer sequences | | |
| Gapdh | gtgttcctaccccaatgtg (SEQ ID NO: 1) | ggtcctcagtgtagcccaag (SEQ ID NO: 2) |
| Camk4 | gagaacctcgtcccggattac (SEQ ID NO: 3) | acacaatggatgtagcacccc (SEQ ID NO: 4) |
| S100a8 | aaatcaccatgccctctacaag (SEQ ID NO: 5) | cccactttatcaccatcgcaa (SEQ ID NO: 6) |
| S100a9 | caccctgagcaagaaggaat (SEQ ID NO: 7) | tgtcatttatgagggcttcattt (SEQ ID NO: 8) |
| Lcn2 | acatttgttccaagctccagggc (SEQ ID NO: 9) | catggcgaactggttgtagtccg (SEQ ID NO: 10) |
| Camp | gctgtggcggtcactatcac (SEQ ID NO: 11) | tgtctagggactgctggttga (SEQ ID NO: 12) |
| Tnfa | actggcagaagaggcactc (SEQ ID NO: 13) | ctggcaccactagttggttg (SEQ ID NO: 14) |
| Tgfb1 | acaattcctggcgttacctt (SEQ ID NO: 15) | agccctgtattccgtctcc (SEQ ID NO: 16) |
| Ifng | atgaacgctacacactgcatc (SEQ ID NO: 17) | ccatccttttgccagttcctc (SEQ ID NO: 18) |
| Il1b | ctgaactcaactgtgaaatgc (SEQ ID NO: 19) | tgatgtgctgctgcgaga (SEQ ID NO: 20) |
| Il10 | gctcttactgactggcatgag (SEQ ID NO: 21) | cgcagctctaggagcatgtg (SEQ ID NO: 22) |
| Il17a | tttaactcccttggcgcaaaa (SEQ ID NO: 23) | ctttccctccgcattgacac (SEQ ID NO: 24) |
| Il17f | aaccagggcatttctgtcccac (SEQ ID NO: 24) | ggcattgatgcagcctgagtgt (SEQ ID NO: 26) |
| Il22 | atgagtttttcccttatgggac (SEQ ID NO: 27) | gctggaagttggacacctcaa (SEQ ID NO: 28) |
| Il23a | atgctggattgcagagcagta (SEQ ID NO: 29) | acggggcacattattttagtct (SEQ ID NO: 30) |
| Ccl2 | ccagcaagatgatcccaatg (SEQ ID NO: 31) | tacgggtcaacttcacattc (SEQ ID NO: 32) |
| Ccl20 | aatctgtgtgcgctgatcca (SEQ ID NO: 33) | ccttgggctgtgtccaattc (SEQ ID NO: 34) |
| Cd36 | atgggctgtgatcggaactg (SEQ ID NO: 35) | tttgccacgtcatctgggttt (SEQ ID NO: 36) |
| Macro | acagagccgattttgaccaag (SEQ ID NO: 37) | cagcagtgcagtacctgcc (SEQ ID NO: 38) |
| Trem2 | ctggaaccgtcaccatcactc (SEQ ID NO: 39) | cgaaactgcatgactcctcgg (SEQ ID NO: 40) |
| Axl | atggccgacattgccagtg (SEQ ID NO: 41) | cggtagtaatcccgttgtaga (SEQ ID NO: 42) |
| Mertk | cagggcctttaccagggaga (SEQ ID NO: 43) | tgtgtgctggatgtgatcttc (SEQ ID NO: 44) |
| Gpnmb | cattcccatctcgaaggtgaaa (SEQ ID NO: 45) | aaatggcagagtcgttgagga (SEQ ID NO: 46) |
| Cd81 | gtggagggctgcaccaaat (SEQ ID NO: 47) | gacgcaaccacagagctaca (SEQ ID NO: 48) |
| Cd51 | gatcgtgttttttcagagtctcca (SEQ ID NO: 49) | tgcagtcaaccccttgaataag (SEQ ID NO: 50) |
| Fcrls | acaggatctaagtgcgtgaatgt (SEQ ID NO: 51) | ctgggtcgttgccctatctg (SEQ ID NO: 52) |
| Cd80 | accccaacataactgagtct (SEQ ID NO: 53) | ttccaaccaagagaagcgagg (SEQ ID NO: 54) |
| Cd86 | tgtttccgtggagacgcaag (SEQ ID NO: 55) | ttgagcctttgtaaatgggca (SEQ ID NO: 56) |
| Nos2 | gttctcagcccaacaatacaaga (SEQ ID NO: 57) | gtggacgggtcgatgtcac (SEQ ID NO: 58) |
| Arg1 | aacacggcagtggctttaacc (SEQ ID NO: 59) | ggttttcatgtggcgcattc (SEQ ID NO: 60) |
| Retnla | ccaatccagctaactatccctcc (SEQ ID NO: 61) | ccagtcaacgagtaagcacag (SEQ ID NO: 62) |
| Chil3 | tctgaaagacaagaacactgagc (SEQ ID NO: 63) | gcaggtccaaacttccatcc (SEQ ID NO: 64) |

-continued

| Gene | Forward primer(5'-3') | Reverse primer(5'-3') |
|---|---|---|
| Human primer sequences | | |
| GAPDH | gtctcctctgacttcaacagcg (SEQ ID NO: 65) | accaccctgttgctgtagccaa (SEQ ID NO: 66) |
| CAMK4 | gttcttcttcgcctctcacatcc (SEQ ID NO: 67) | ctgtgacgagttctaggaccag (SEQ ID NO: 68) |
| S100A8 | atgccgtctacagggatgacct (SEQ ID NO: 69) | agaatgaggaactcctggaagtta (SEQ ID NO: 70) |
| S100A9 | gcacccagacaccctgaacca (SEQ ID NO: 71) | tgtgtccaggtcctccatgatg (SEQ ID NO: 72) |
| CAMP | gacacagcagtcaccagaggat (SEQ ID NO: 73) | tcacaactgatgtcaaaggagcc (SEQ ID NO: 74) |
| DEFB4A | ataggcgatcctgttacctgcc (SEQ ID NO: 75) | catcagccacagcagcttcttg (SEQ ID NO: 76) |
| SPRR2A | gttccacagctccaccttca (SEQ ID NO: 77) | cacagcccaggacttcctttt (SEQ ID NO: 78) |
| SPRR2B | actggttaatcctgagactccagc (SEQ ID NO: 79) | aggaggatatttctgctggcac (SEQ ID NO: 80) |
| IL1B | ccacagaccttccaggagaatg (SEQ ID NO: 81) | gtgcagttcagtgatcgtacagg (SEQ ID NO: 82) |
| IL6 | aaattcggtacatcctcgacggca (SEQ ID NO: 83) | agtgcctctttgctgctttcacac (SEQ ID NO: 84) |
| IL10 | gactttaagggttacctgggttg (SEQ ID NO: 85) | tcacatgcgccttgatgtctg (SEQ ID NO: 86) |
| IL12B | gacattctgcgttcaggtccag (SEQ ID NO: 87) | cattttttgcggcagatgaccgtg (SEQ ID NO: 88) |
| IL17A | agattactacaaccgatccacct (SEQ ID NO: 89) | ggggacagagttcatgtggta (SEQ ID NO: 90) |
| IL23A | gagccttctctgctccctgata (SEQ ID NO: 91) | gactgaggcttggaatctgctg (SEQ ID NO: 92) |
| TNFA | ctcttctgcctgctgcactttg (SEQ ID NO: 93) | atgggctacaggcttgtcactc (SEQ ID NO: 94) |
| TGFB1 | caattcctggcgataccttcag (SEQ ID NO: 95) | gcacaactccggtgacatcaa (SEQ ID NO: 96) |
| CCL2 | agaatcaccagcagcaagtgtcc (SEQ ID NO: 97) | tcctgaacccacttctgcttgg (SEQ ID NO: 98) |
| CCL20 | aagttgtctgtgtgcgcaaatcc (SEQ ID NO: 99) | ccattccagaaaagccacagtttt (SEQ ID NO: 100) |

| Amplification system | |
|---|---|
| Reagent | Addition |
| SYBR Premix Ex Taq II (2×) | 10 μL |
| Forward Primer (10 μM) | 0.8 μL |
| Reverse Primer (10 μM) | 0.8 μL |
| cDNA | 1 μL |
| dH$_2$O | 7.4 μL |

| Amplification program | | |
|---|---|---|
| First step | Second step | Melting curve |
| 95° C., 10 s | 95° C., 15 s | 95° C., 15 s |
| | 60° C., 40 s | 60° C., 1 min |
| | 40 cycles | 95° C., 15 s |

4) Expression Detected by Flow Cytometry (FCM) of CaMK4

1 ml of anticoagulation was taken into 15 ml centrifuge tube, 5 ml of red blood cell lysate was added, mixed and lysed on ice for 5 min (appropriate mixing once in between), thereby obtaining lysed solution. The reaction was terminated by filling PBS, the lysed solution was centrifuged at 500 g for 10 min at 4° C., cell precipitation was collected, rinsing once in PBS, and cells were collected. After cell counting, 1×10$^6$ cells were taken, and after blocking Fc receptor, antibodies V500-CD45, PerCP/Cy5.5-CD3, FITC-CD4, PE/Cy7-CD8, and PE-CD14 were added for surface markers staining. Then, the cells were fixed and broken, and rabbit anti-human CaMK4 antibody and AF647-labeled goat anti-rabbit IgG second antibody were added sequentially. After tH&E staining was completed, the cells were rinsing once in PBS, resuspended by adding 200 L, PBS, and detected by flow cytometry.

5) Expression Detected by Immunohistochemistry of CaMK4 in Skin

After paraffin sections were dewaxed, antigen retrieval was performed with 0.01 molarities (M) (pH=6.0) sodium citrate. Endogenous peroxidase was blocked with 3% H$_2$O$_2$ and nonspecific proteins were blocked by confining liquid. First antibody (i.e., CaMK4 antibody) was incubated overnight at 4° C. and the second antibody was incubated at 37° C. for 30 min, color development was performed with diaminobenzidine (DAB), nuclei were stained with hematoxylin, dried, and sealed.

Figure 2:
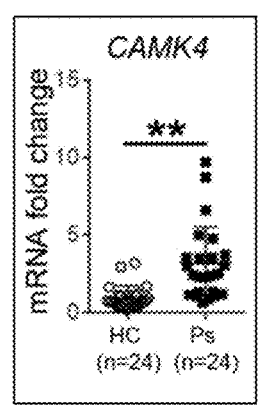
FIG. 2 shows mRNA levels of CaMK4 detected by quantitative PCR in peripheral blood of healthy control group (n=24) and psoriasis patients (n=24).
Figures 3A, 3B:
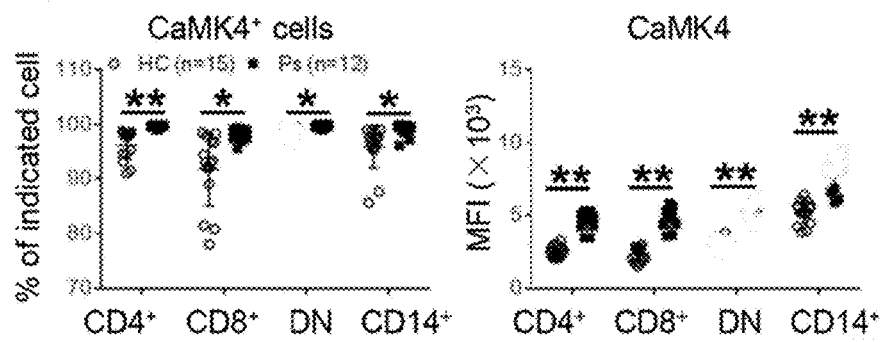
FIG. 3a shows proportion of CaMK4 indicated cells of T cell subsets (including CD4$^+$, CD8$^+$, DN cells) and CD14$^+$ monocytes in peripheral blood of healthy control group (n=15) and psoriasis patients (n=12) detected by flow cytometry.
FIG. 3b shows mean fluorescence intensity (MFI) of CaMK4 of T cell subsets (CD4$^+$, CD8$^+$, DN cells) and CD14$^+$ monocytes in peripheral blood of healthy control group (n=15) and psoriasis patients (n=12) detected by flow cytometry.
Figure 7:
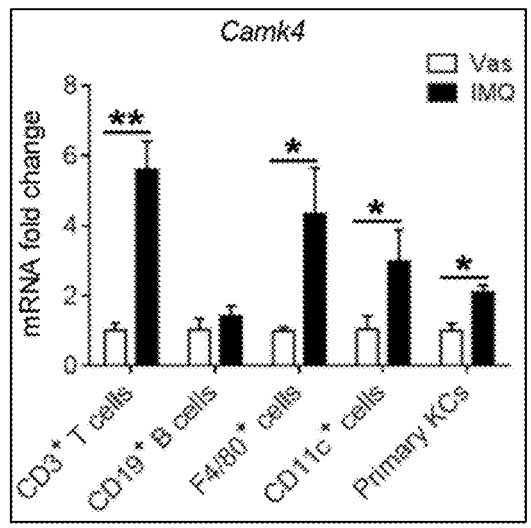
FIG. 7 shows mRNA levels of CaMK4 detected by quantitative PCR in CD3$^+$ T cells, CD19$^+$ B cells, F4/80$^+$ cells and CD11c$^+$ cells of mouse skin sorted by magnetic beads; where 5-7 mouse skin tissues were used as a sample for magnetic bead sorting, data represents an independent experiment with 3 samples in each group, expressed as mean±standard deviation, *p<0.05, **p<0.01.

Referring to FIGS. 1-7, CaMK4 was increased significantly in psoriasis patients and induced skin lesions in mice. Compared with healthy control groups, the mRNA levels of CaMK4 in peripheral blood of patients with psoriasis were also elevated, with the highest expression intensity in CD14+ monocytes and a positive correlation with IL1B and IL12B expression. The protein levels and mRNA levels of CaMK4 were significantly increased in CD3$^+$ T cells, F4/80$^+$ cells, CD11c$^+$ cells and KCs after IMQ induction, as revealed by sorting of immune cell subsets in mouse skin and isolation of keratinocytes.

EXAMPLE 2

Using the mouse model constructed in the example 1, skin samples were collected on the 5th day for experiment.

1) The back skin thickness, scaling and erythema development of mice were observed on days 0 -5 after applying IMQ to the shaved back skin of mice. According to the clinical psoriasis area and severity index, the severity of back skin was evaluated by thickness, scaling and erythema. The back skin thickness was measured with vernier calipers. Scaling and erythema were scored on a scale ranging from 0-4: 0 represents none; 1 represents mild; 2 represents moderate; 3 represents significant; and 4 represents very significant.

2) Skin sections were prepared for staining with H&E, and the skin sections were stained by using the conventional universal H&E staining method.

3) Statistical analysis of epidermal thickness. Specifically, H&E-stained sections were photographed in a double-blind manner and then measured for epidermal thickness.

4) RNA sequencing analysis of whole skin of CaMK4$^{+/+}$ (n=3) and CaMK4$^{-/-}$ (n=3) mice induced by IMQ. Specifically, the back skin of mice was isolated, frozen at −80° C. in the size of soybean particles and sent to Lc-bio technologies (Hangzhou) Co., Ltd, China, for RNA sequencing.

5) The mRNA levels of IMQ induced mouse skin pathogenic factors were detected by quantitative PCR. The method was the same as that in the example 1.

Figure 8:
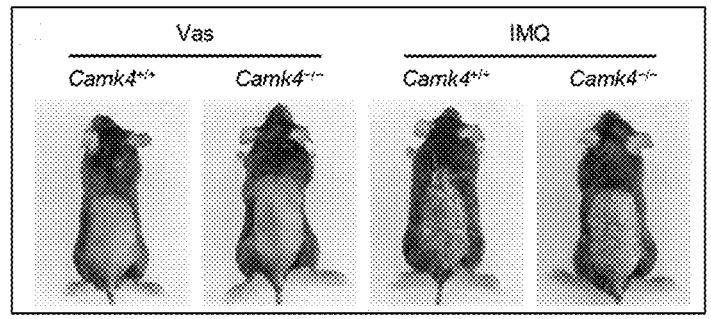
FIG. 8 is a representative picture showing mouse back skin of CaMK4$^{-/-}$ mice and CaMK4$^{+/+}$ mice.
Figures 9A, 9B, 9C:
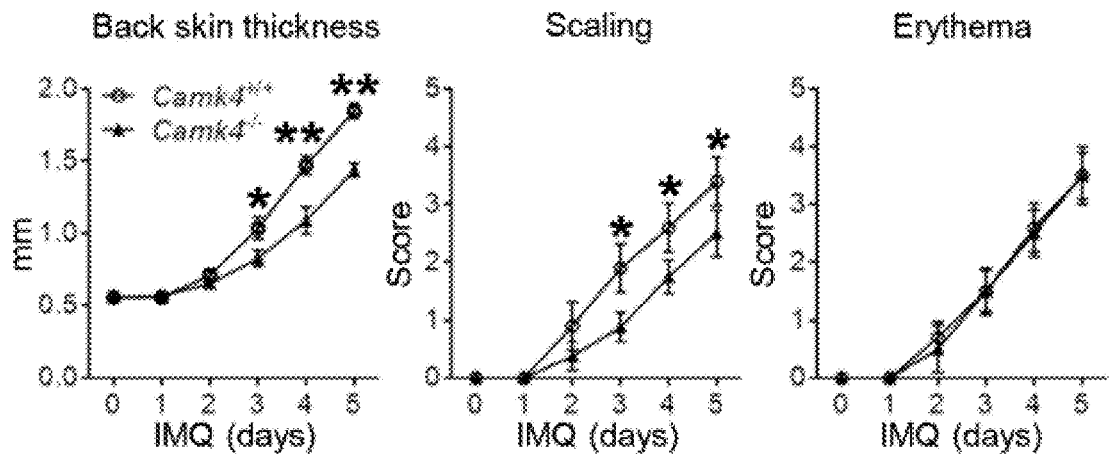
FIG. 9a shows scoring curves of back skin thickness of CaMK4$^{-/-}$ mice and CaMK4$^{+/+}$ mice.
FIG. 9b shows scoring curves of scaling of CaMK4$^{-/-}$ mice and CaMK4$^{+/+}$ mice.
FIG. 9c shows scoring curves of erythema of CaMK4$^{-/-}$ mice and CaMK4$^{+/+}$ mice.
Figure 10:
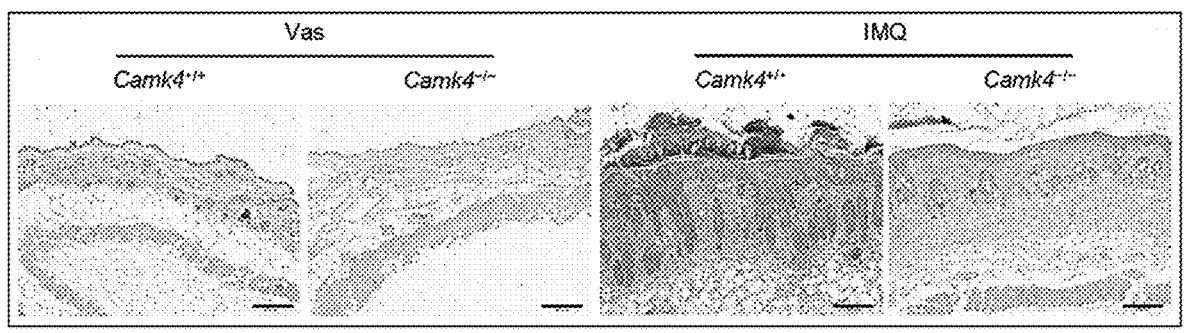
FIG. 10 shows hematoxylin-eosin (H&E) staining of skin sections of CaMK4$^{-/-}$ mice and CaMK4$^{+/+}$ mice (scale bar: 200 μm).
Figure 11:
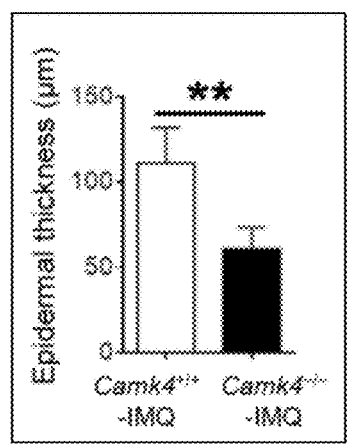
FIG. 11 shows a result of statistical analysis of epidermal thickness of IMQ induced CaMK4$^{-/-}$ mice and CaMK4$^{+/+}$ mice.
Figure 12:
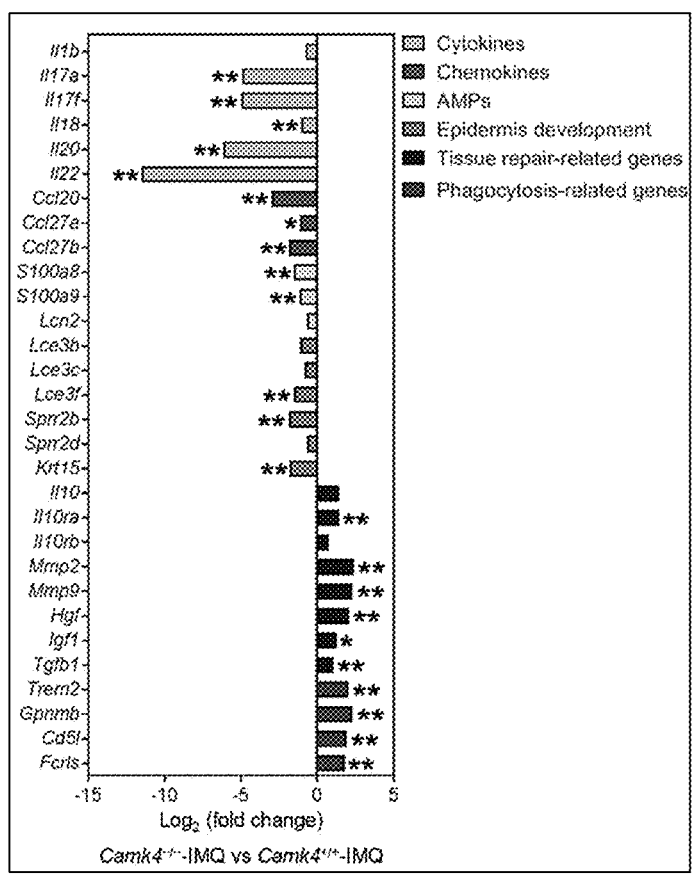
FIG. 12 shows results of RNA sequencing analysis of whole skin of IMQ induced CaMK4$^{+/+}$ (n=3) mice and CaMK4$^{-/-}$ (n=3) mice.
Figure 13:
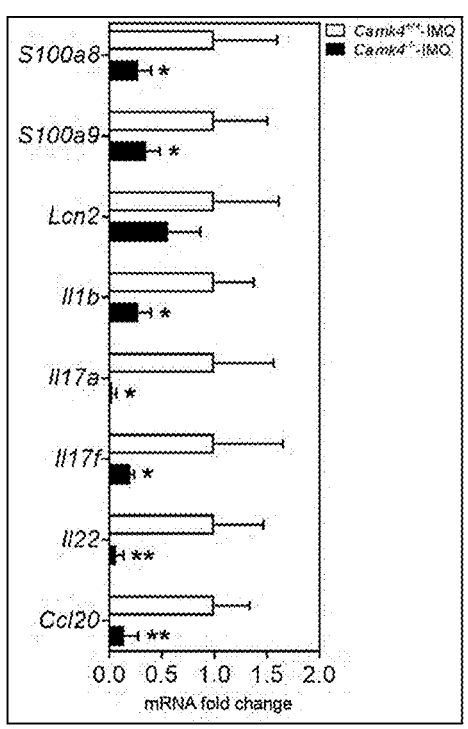
FIG. 13 shows mRNA levels detected by quantitative PCR of skin pathogenic factors induced by IMQ; where data represent twice independent experiments with 7-8 mice in each group, expressed as mean±standard deviation, *p<0.05, **p<0.01.

Referring to FIGS. 8-13, the psoriasiform phenotype of CaMK4$^{-/-}$ mice was less than that of CaMK4$^{+/+}$ mice, including skin thickness, scaling and epidermal thickness. Moreover, the mRNA levels of proinflammatory cytokines, chemokines, antimicrobial peptides (AMPs) and epidermis development genes in the skin lesions of CaMK4$^{-/-}$ mice were reduced compared with those of CaMK4$^{+/+}$ mice, and the mRNA levels of tissue repair-related genes and phagocytosis-related genes were increased compared with those of CaMK4$^{+/+}$ mice.

EXAMPLE 3

IMQ triggers psoriasiform inflammation via TLR7, which is expressed on a variety of bone marrow-derived natural immune cells. Moreover, IMQ induces upregulation of CaMK4 in F4/80$^+$ and CD11c$^+$ cells of mouse skin (with reference to the example 1). Therefore, the changes of specific skin myeloid cell subsets were further detected. Firstly, immune cells were isolated as follows.

On the 5th day after continuous application of IMQ, the back skin of mice was separated, then cut into small pieces and placed in a Roswell Park memorial institute (RPMI) 1640 medium containing 1 milligram per milliliter (mg/mL) of collagenase IV, 50 micrograms per milliliter (μg/mL) of deoxyribonuclease (DNase) I, 10 millimoles per liter (mM) of 24442-hydroxyethyl)piperazin-1-yl)ethanesulfonic acid (HEPES) and 10% of PBS, and digested at 37° C. for 90 mM The digested tissue was filtered through a 74 μm nylon mesh to remove tissue fragments, and additional RPMI 1640 was added to the suspension to inactivate the enzyme activity. Skin leukocytes were obtained by centrifugation with 30% and 70% percoll at 1260 g for 20 min and aspirating the middle white cloudy layer. After rinsing with PBS, the cells (i.e., skin leukocytes) were counted. After cell counting, 1×10$^6$ cells were taken, and after blocking the Fc receptor, antibodies PerCP/Cy5.5-CD45, V450-CD11b, FITC-Ly6C, PE-CD11 c, PE/Cy7-F4/80, APC-Ly6G, APC/Cy7-MHC II were added for surface marker staining. After the staining was completed, the cells were rinsed once in PBS, 200 μL PBS was added to resuspend the cells and detected by flow cytometry.

Figure 14A:
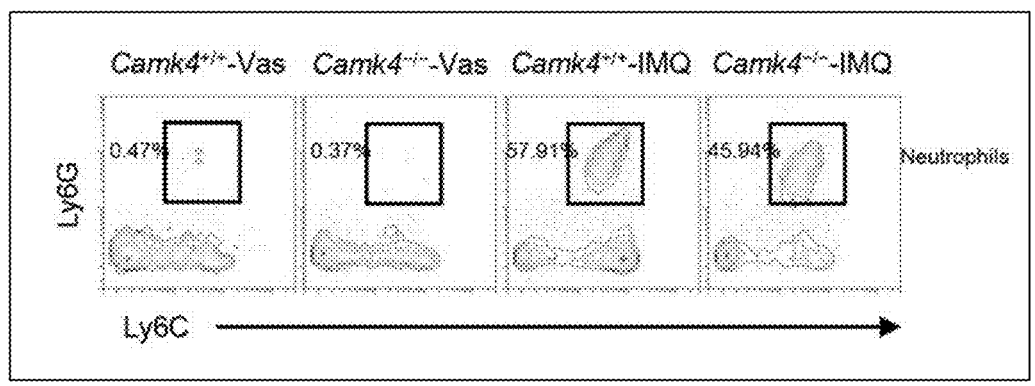
FIGS. 14a-14b show results of statistical analysis of proportion and number of neutrophils in mouse skin.
Figure 14B:
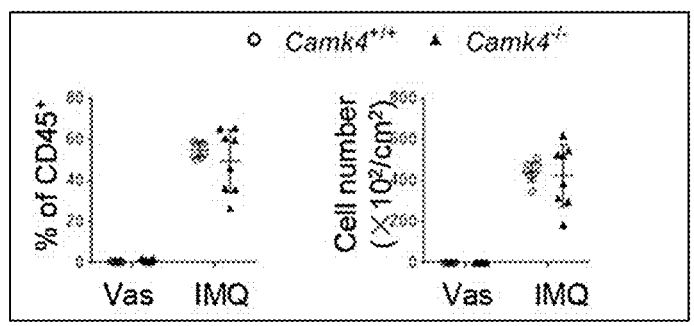
Figure 15A:
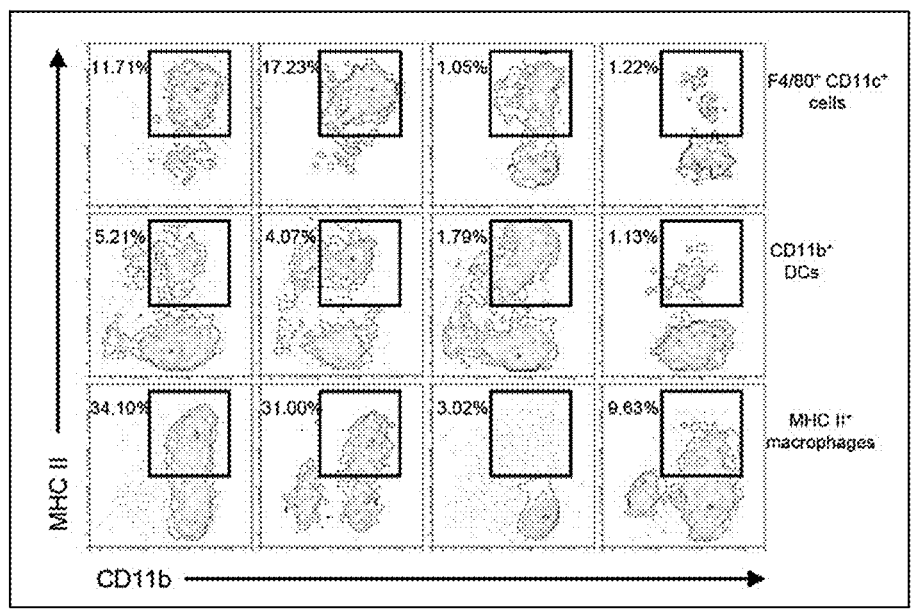
FIGS. 15a-15b show results of statistical analysis of proportions and numbers of F4/80$^+$ CD11c$^+$ cells, CD11b$^+$ DCs and MHC II$^+$ macrophages in mouse skin.
Figure 15B:
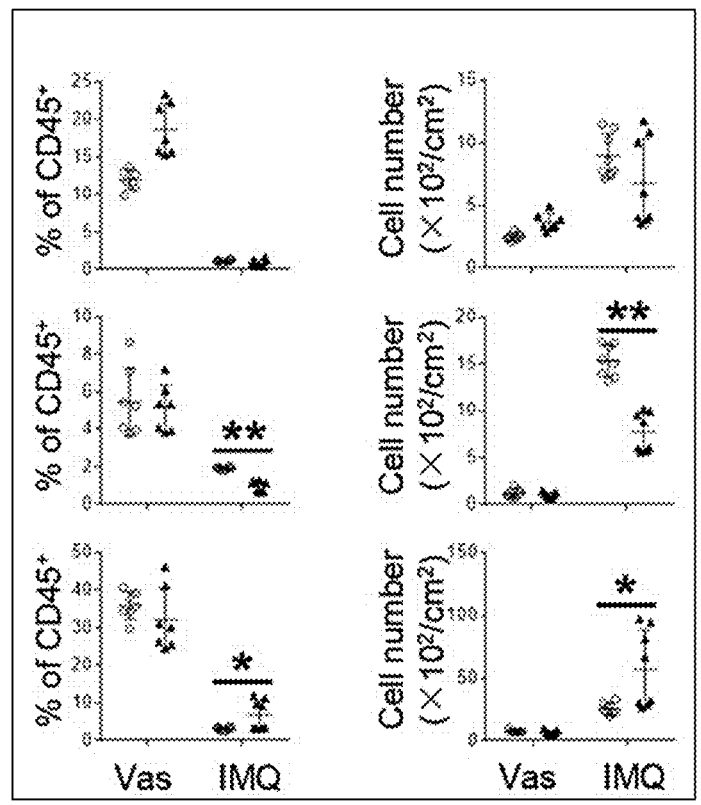
Figure 16A:
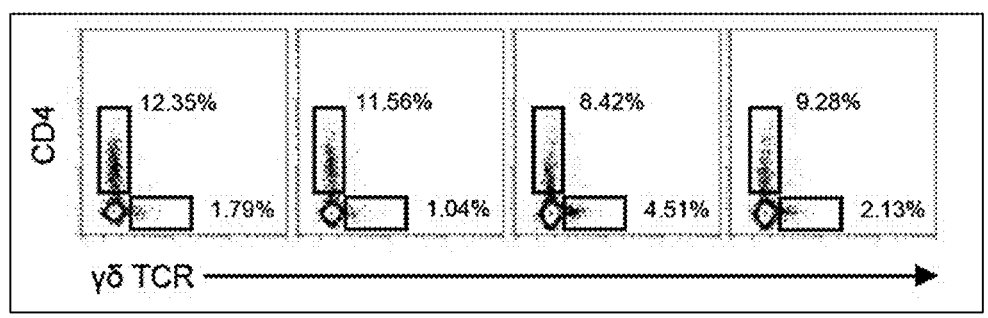
FIGS. 16a-16b show results of statistical analysis of proportions and numbers of CD4$^+$ T cells and γδ TCR$^+$ T cells in mouse skin.
Figure 16B:
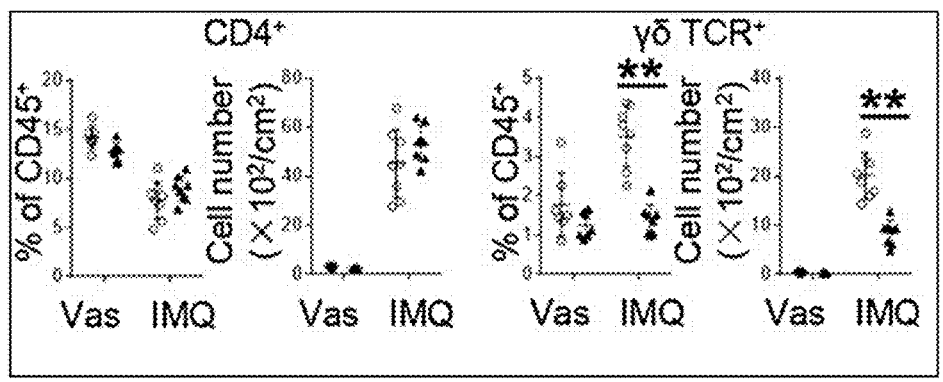
Figure 17A:
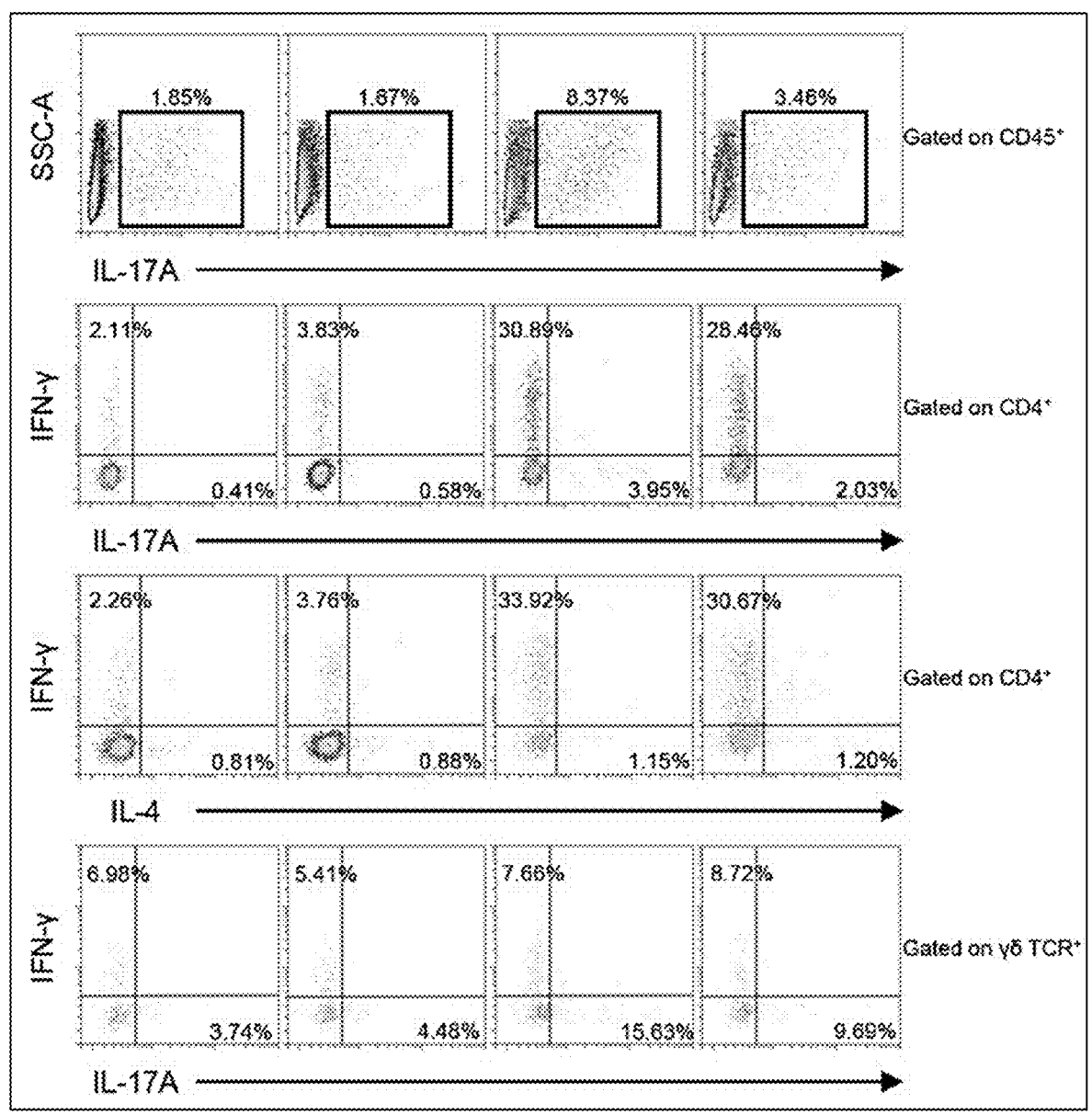
FIGS. 17a-17b show results of statistical analysis of proportions and numbers of IL-17A$^+$ CD45$^+$ cells, IFN-γ$^+$ CD4$^+$ cells, IL-17A$^+$ CD4$^+$ cells, IL-4$^+$ CD4$^+$ cells, IFN-γ$^+$ γδ TCR$^+$ cells, IL-17A$^+$ γδ TCR$^+$ cells in mouse skin; where data represent twice independent experiments with 7-8 mice in each group, expressed as mean±standard deviation, *p<0.05, **p<0.01.
Figure 17B:
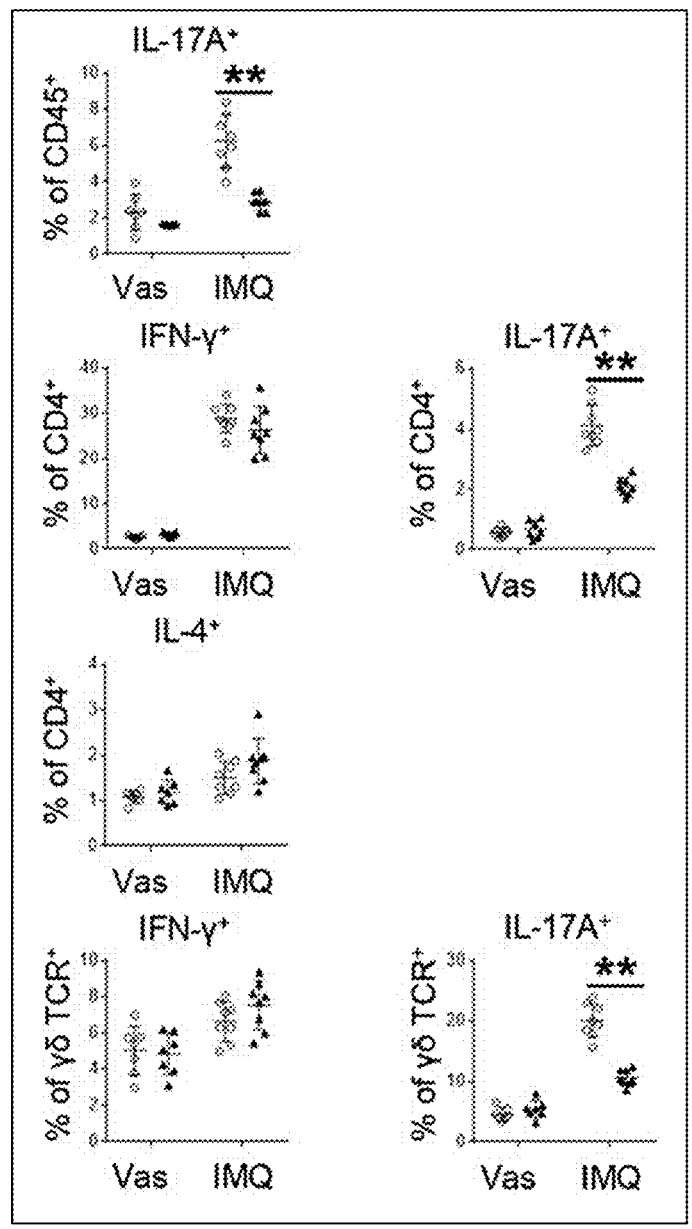

Referring to FIGS. 14-17, compared with CaMK4$^{+/+}$ mice, CD11b$^+$ DCs in the skin of IMQ induced CaMK4$^{-/-}$ mice were significantly decreased, while MHC II$^+$ macrophages were significantly increased.

Detection of CD4$^+$ T cell subsets and γδ T cell subsets showed that IL-17A$^+$ CD45$^+$ cells, IL-17A$^+$ CD4$^+$ cells and IL-17A$^+$ γδTCR$^+$ cells were reduced in the skin of IMQ-induced Camk4$^{-/-}$ mice compared to Camk4$^{+/+}$ mice. It was also found that after IMQ induction, IL-17A mainly came from γδ TCR$^+$ cells, while IFN-γ mainly from CD4$^+$ T cells.

EXAMPLE 4

Macrophages play a regulatory role mainly by producing IL-10. IL-10 is a central anti-inflammatory mediator, which can reduce tissue damage caused by excessive and uncontrolled inflammatory stimulation and protect the host from excessive inflammatory response. To determine whether macrophages produce IL-10 and participate in alleviating psoriasis symptoms of CaMK4 deficiency, the expressions of IL-10 in skin and macrophages were first detected.

1) The mRNA levels of IL-10 in mouse skin were detected by quantitative PCR, and the method was the same as that in the example 1.

2) The expression of IL-10 in mouse skin was detected by immunohistochemistry, and the method was the same as that in the example 1.

3) F4/80, IL-10 and DAPI in mouse skin were detected by immunofluorescence. After paraffin sections were dewaxed, antigen retrieval was performed with 0.01 molarities (M) (pH=6.0) sodium citrate. Endogenous peroxidase was blocked with 3% H$_2$O$_2$ and nonspecific proteins were blocked by confining liquid. First antibody (i.e., F4/80 and IL-10 antibody) was incubated overnight at 4° C. and the second antibody was incubated at 37° C. for 30 min, nuclei were stained with DAPI, and sealed with anti-fluorescence quenching sealing solution.

4) The expressions of IL-10 in F4/80+ CD11c+ cells, CD11b+ DCs and MHC II+ macrophages were detected by flow cytometry. The method was the same as that in the example 3.

Figure 18:
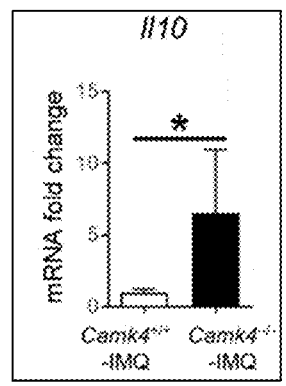
FIG. 18 shows mRNA levels detected by quantitative PCR of IL10 in mouse skin of IMQ induced CaMK4$^{-/-}$ mice and CaMK4$^{+/+}$ mice.
Figure 19:
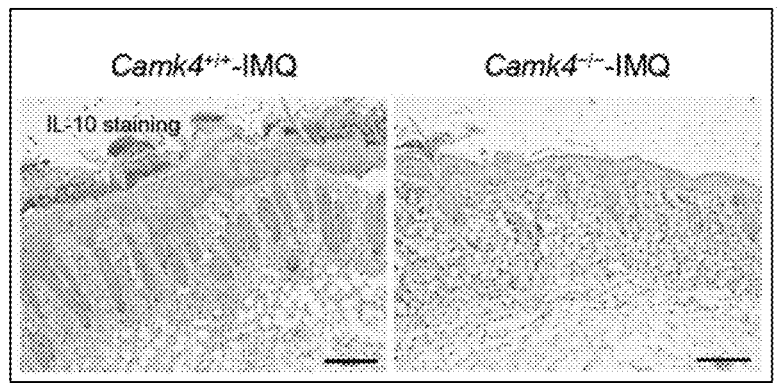
FIG. 19 shows expression detected by immunohistochemistry of IL-10 in mouse skin of IMQ induced CaMK4$^{-/-}$ mice and CaMK4$^{+/+}$ mice (scale bar: 200 μm).
Figure 20:
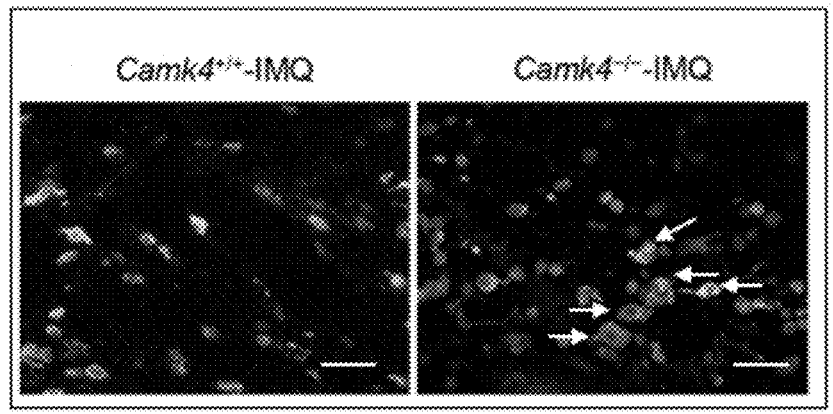
FIG. 20 shows a result detected by immunofluorescence of F4/80, IL-10 and DAPI in mouse skin of IMQ induced CaMK4$^{-/-}$ mice and CaMK4$^{+/+}$ mice (scale bar: 50 μm); where a solid arrows show dermal F4/80$^+$ IL-10$^+$ cells.
Figure 21:
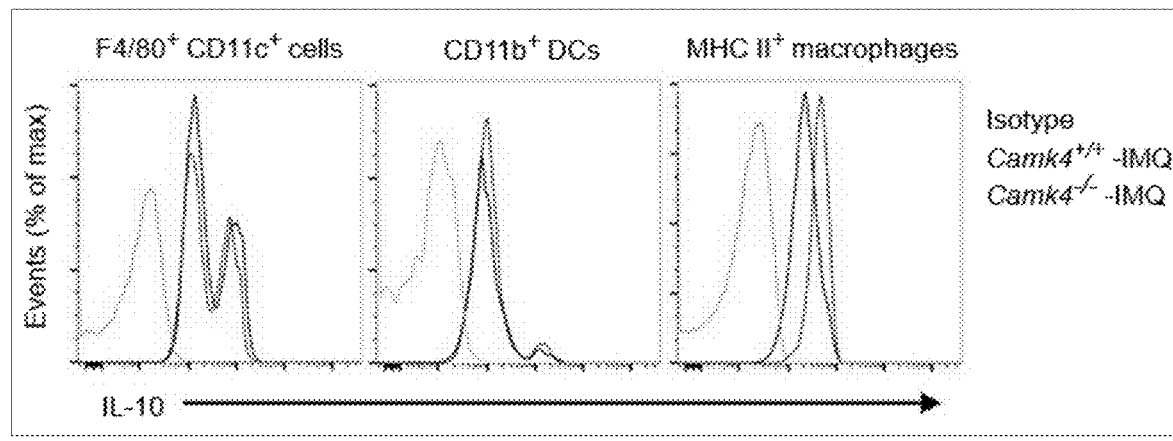
FIG. 21 shows expressions detected by flow cytometry of IL-10 in F4/80$^+$ CD11c+ cells, CD11b$^+$ DCs and MHC II$^+$ macrophages of IMQ induced CaMK4$^{-/-}$ mice and CaMK4$^{+/+}$ mice.
Figure 22:
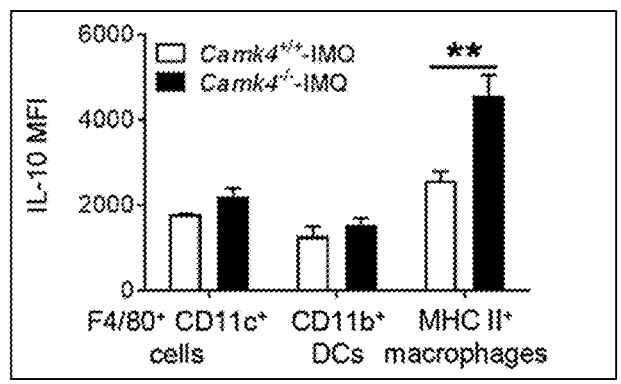
FIG. 22 shows results of statistical analysis of MFI of IL-10; where data represent twice independent experiments with 7-8 mice in each group, expressed as mean±standard deviation, *p<0.05, **p<0.01.

Referring to FIG. 18-22, a result of quantitative PCR showed that the mRNA level of IL-10 in the skin of IMQ induced CaMK4$^{-/-}$ mice was higher than that of CaMK4$^{+/+}$ mice. A result of immunohistochemistry showed that the protein level of IL-10 in the skin of CaMK4$^{-/-}$ mice was significantly higher than that of CaMK4$^{+/+}$ mice. Results of immunofluorescence and flow cytometry showed that IL-10 mainly came from dermal macrophages.

EXAMPLE 5

Determination of Cytokines in Macrophages

Bone marrow cells were rinsed from the tibia and femur of mice and cultured in a RPMI 1640 medium containing 10% FBS, 1% of antibiotics and 10 nanograms per milliliter (ng/ml) M-CSF. The medium was changed every 2 days for 6 consecutive days, so that BMDMs can be obtained. BMDMs were treated for 6 h with an inhibitor that is one selected from a group consisting of CaMK4 10 μM KN-93, ADCY1 inhibitor 20 μM ST034307, 2 μg/ml cAMP, MEK1/2 inhibitor 20 μM U0126 , and p38 inhibitor 20 μM SB203580; and then stimulated with 2 μg/ml IMQ for 12 h to extract protein and RNA, or stimulated for 24 h to determine cytokines.

1) The protein levels of CaMK4, ADCY1, p-Erk1/2, Erk1/2, p-p38, p38 in BMDMs treated with different inhibitors were detected by Western blot. Protein samples were obtained by lysing the cells (i.e., bone marrow cells)with radio immunoprecipitation assay (RIPA) lysis buffer containing a mixture of phenylmethylsulfonyl fluoride (PMSF), protease inhibitor and phosphatase inhibitor. After quantification of proteins, 10% sodium dodecyl sulfate-polyacrylamide (SDS-PAGE) gel electrophoresis was performed. The proteins in the gel were transferred to the nitrocellulose membranes; first antibody and second antibody were incubated, and color development was performed with an electrochemiluminescence (ECL) solution.

2) The mRNA levels of IL-10 in BMDMs treated with different inhibitors were detected by quantitative PCR. The method was the same as that in the example 1.

3) The contents of IL-10 in BMDMs supernatant treated with different inhibitors were detected by ELISA according to the standard method in the manufacturer's instructions.

4) The mRNA levels of macrophage phenotypic markers (including M1 and M2) and phagocytosis-related genes in IMQ stimulated CaMK4$^{+/+}$ and CaMK4$^{-/-}$ BMDMs were detected by quantitative PCR. The method was the same as that in the example 1.

5) The protein expression levels, IL-10 mRNA levels, IL-10 contents and cytokine mRNA levels in peripheral blood CD14$^+$ monocytes of patients with psoriasis (n=3) were determined by using the methods described above.

Figure 23:
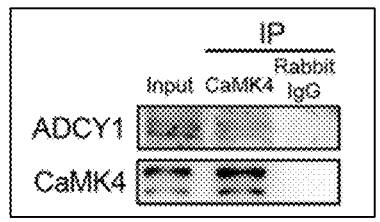
FIG. 23 shows interaction between CaMK4 and AKT in BMDMs detected by co-immunoprecipitation.
Figure 24:
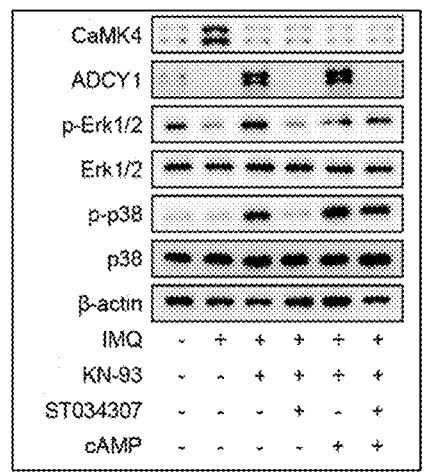
FIG. 24 shows protein levels detected by Western blot of CaMK4, ADCY1, p-Erk1/2, Erk1/2, p-p38 and p38 in BMDMs respectively treated with IMQ, KN-93, ST034307 and cAMP.
Figure 25:
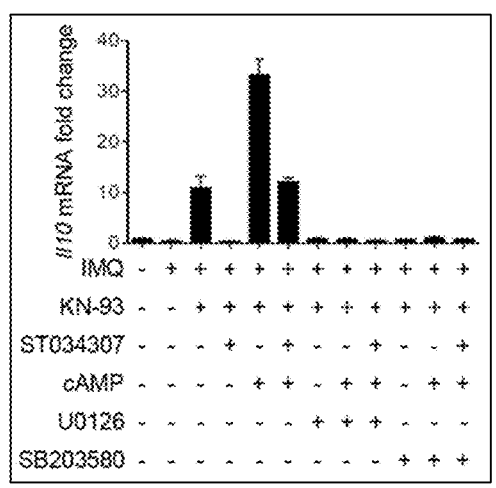
FIG. 25 shows mRNA levels detected by quantitative PCR of IL10 in BMDMs respectively treated with IMQ, KN-93, ST034307, cAMP, U0126 and SB203580.
Figure 26:
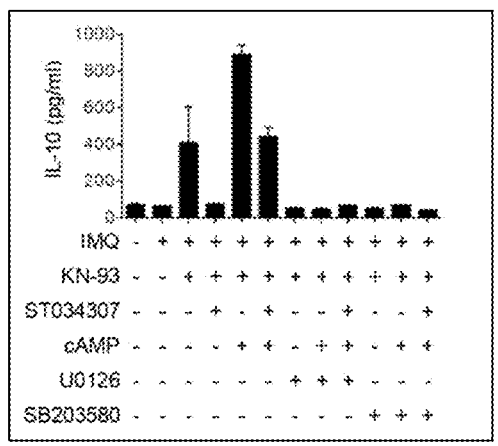
FIG. 26 shows contents detected by enzyme linked immunosorbent assay (ELISA) of IL-10 in BMDMs supernatant respectively treated with IMQ, KN-93, ST034307, cAMP, U0126 and SB203580.
Figure 27:
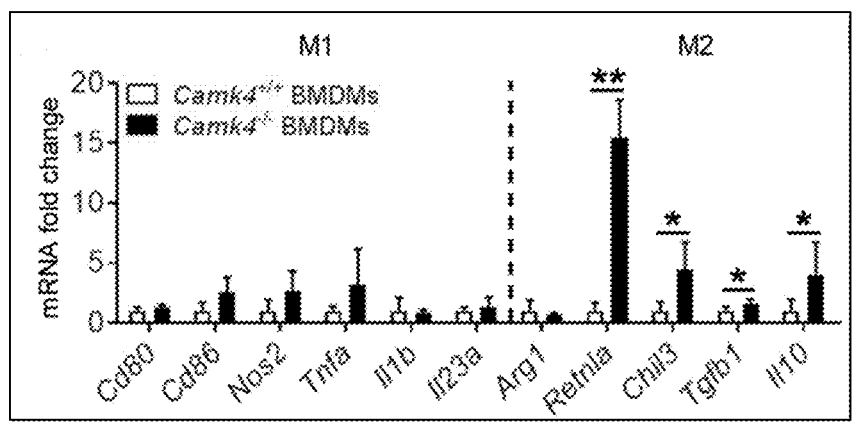
FIG. 27 shows mRNA levels of macrophage phenotypic markers (including M1 and M2) in IMQ stimulated CaMK4$^{+/+}$ and CaMK4$^{-/-}$ BMDMs detected by quantitative PCR after 12 hours of RNA extraction with 2 ng/mL IMQ.
Figure 28:
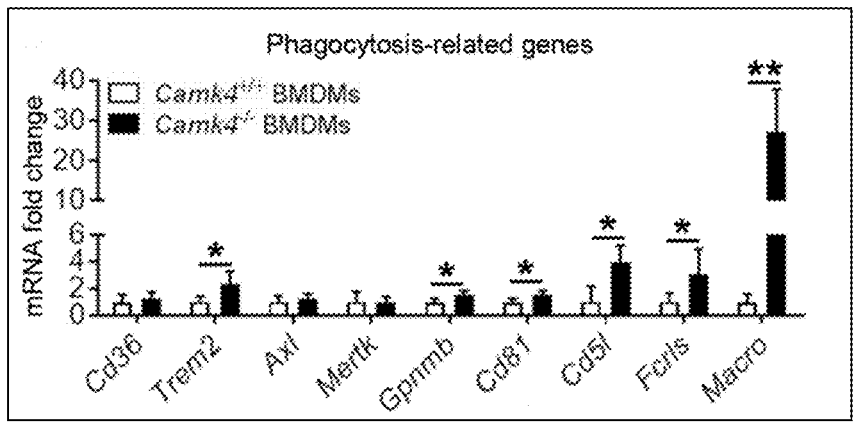
FIG. 28 shows mRNA levels of phagocytosis-related genes in IMQ stimulated CaMK4$^{+/+}$ and CaMK4$^{-/-}$ BMDMs detected by quantitative PCR after 12 hours of RNA extraction with 2 ng/mL IMQ.
Figure 29:
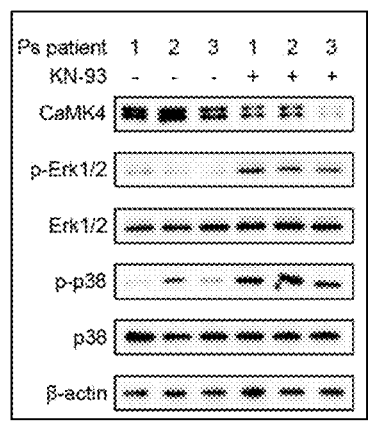
FIG. 29 shows protein levels of CaMK4, p-Erk1/2, Erk1/2, p-p38, p38 in monocytes detected by Western blot after treatment of peripheral blood CD14+ monocytes from magnetic bead-sorted psoriasis patients (n=3) with CaMK4 inhibitor 10 μM KN-93, MEK1/2 inhibitor 20 μM U0126, and p38 inhibitor 20 μM SB203580 for 12 h for protein extraction.
Figure 30:
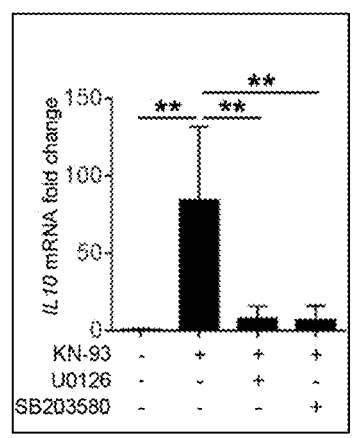
FIG. 30 shows mRNA levels of IL10 in monocytes detected by quantitative PCR after treatment of peripheral blood CD14+ monocytes from magnetic bead-sorted psoriasis patients (n=3) with CaMK4 inhibitor 10 μM KN-93, MEK1/2 inhibitor 20 μM U0126, and p38 inhibitor 20 μM SB203580 for 12 h for RNA extraction.
Figure 31:
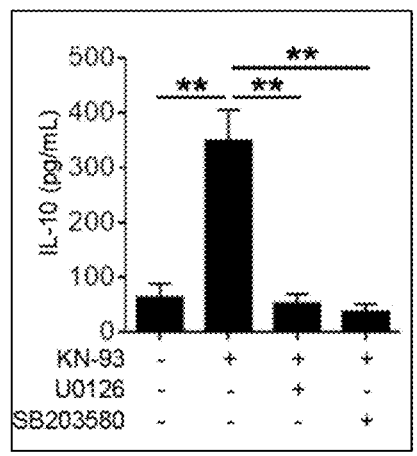
FIG. 31 shows content of IL-10 in monocyte supernatant detected by ELISA after treatment of peripheral blood CD14+ monocytes from magnetic bead-sorted psoriasis patients (n=3) with CaMK4 inhibitor 10 μM KN-93, MEK1/2 inhibitor 20 μM U0126, and p38 inhibitor 20 μM SB203580.
Figure 32:
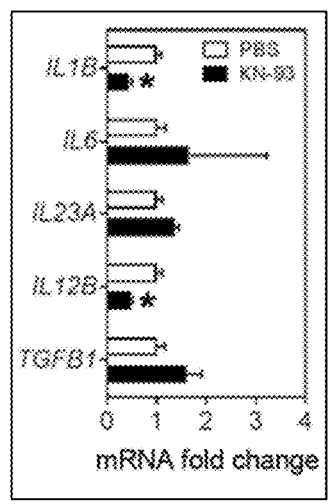
FIG. 32 shows mRNA levels of monocyte cytokines detected by quantitative PCR after treatment of peripheral blood CD14+ monocytes from magnetic bead-sorted psoriasis patients (n=3) with CaMK4 inhibitor 10 μM KN-93, MEK1/2 inhibitor 20 μM U0126, and p38 inhibitor 20 μM SB203580 for 24 h for cytokine determination; where data represent three times independent experiments, expressed as mean±standard deviation, *p<0.05, **p<0.01.

Referring to FIGS. 23-32, in vitro experiments revealed that inhibition of CaMK4 BMDMs restored IL-10 production by upregulating ADCY1-cAMP-Erk1/2 and p38 pathways; inhibition of CaMK4 upregulated the expression of M2 genes and phagocytosis-related genes, and demonstrated that CaMK4 downregulation of ADCY1-cAMP-Erk1/2 and p38 pathways inhibited IL-10 production by macrophages and CaMK4 inhibited M2 macrophage polarization and phagocytosis. Similarly, inhibition of CaMK4 in peripheral monocytes from patients with psoriasis restored IL-10 production and downregulated the expression of proinflammatory cytokines.

EXAMPLE 6

Exogenous Repletion of IL-10 and Camk4-/-BMDM in Mice In Vivo by Adoptive Transfer 62.5 mg of IMQ were applied to the shaved back skin of wild-type (WT) mice for 5 days. IL-10 (1 μg per mouse) or PBS was injected into mice through tail vein on 1 h before IMQ application on day 0 and day 2. Samples were collected on day 5 for subsequent experiments.

62.5 mg of IMQ were applied to the shaved back skin of wild-type mice for 5 days. 1×10$^6$ CaMK4$^{+/+}$ BMDMs or CaMK4$^{-/-}$ BMDMs were injected into mice through tail vein on 1 h before IMQ application on day 0. Samples were collected on day 5 for subsequent experiments.

1) The back skin thickness, scaling and erythema development of mice were observed on days 0 -5 after applying IMQ to the shaved back skin of mice, and scored. The method is the same as that in the example 2;

2) Statistical analysis of epidermal thickness was performed; the method is the same as that in the example 2.

3) The mRNA levels of IMQ induced mouse skin pathogenic factors were detected by quantitative PCR. The method was the same as that in the example 1.

Figure 33:
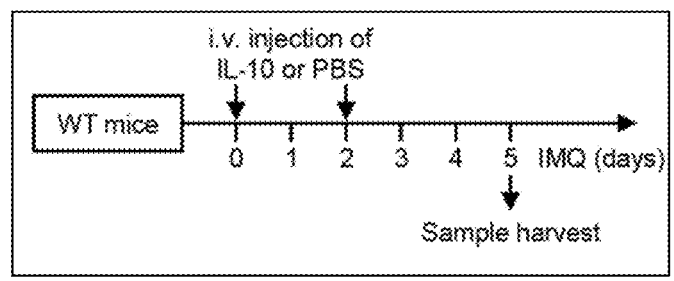
FIG. 33 is a schematic diagram of therapeutic model of mice injected IL-10 or phosphate buffer saline (PBS) in vivo.
Figure 34:
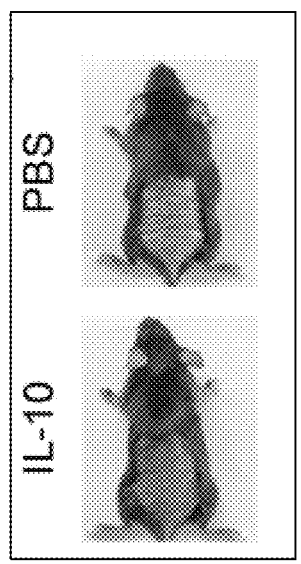
FIG. 34 is a representative picture showing back skin of mice injected with PBS or IL-10.
Figure 35A:
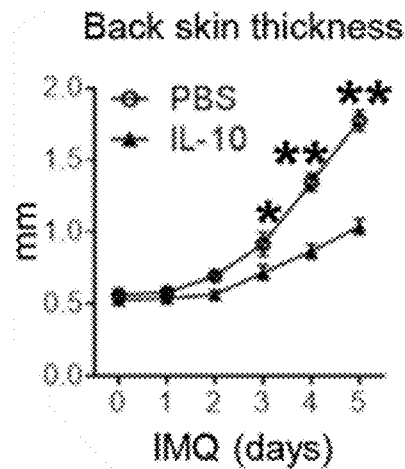
FIG. 35a shows scoring curves of back skin thickness of mice injected PBS or IL-10 in vivo.
Figure 35B:
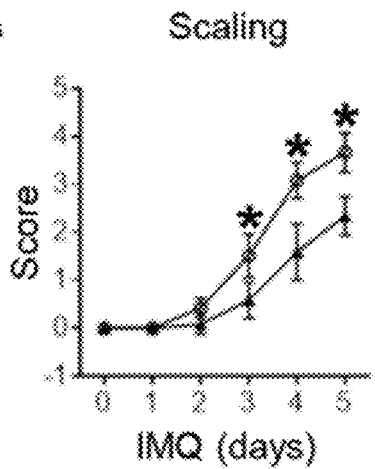
FIG. 35b shows scoring curves of scaling of mice injected PBS or IL-10 in vivo.
Figure 35C:
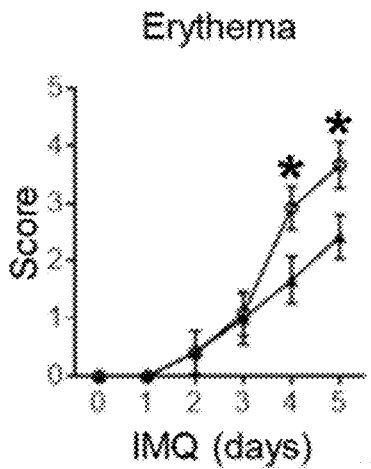
FIG. 35c shows scoring curves of erythema of mice injected PBS or IL-10 in vivo.
Figure 36:
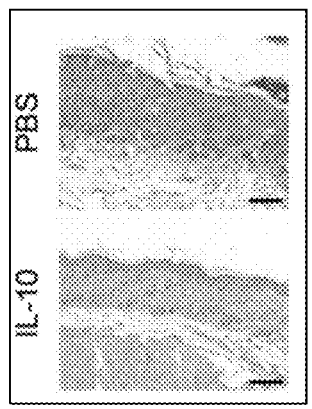
FIG. 36 shows H&E staining of skin sections of mice injected PBS or IL-10 in vivo (scale bar: 200 μm).
Figure 37:
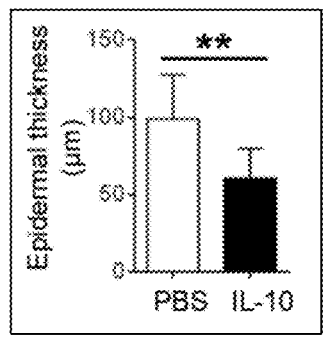
FIG. 37 shows a result of statistical analysis of epidermal thickness of mice injected PBS or IL-10 in vivo.
Figure 38:
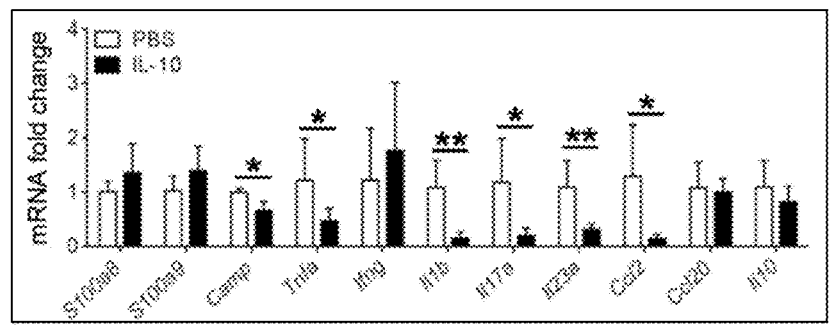
FIG. 38 shows mRNA levels detected by quantitative PCR of skin pathogenic factors of mice injected PBS or IL-10 in vivo induced by IMQ.
Figure 39:
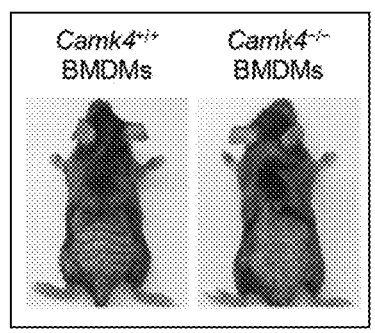
FIG. 39 is a representative picture showing back skin of mice injected of 1×10$^6$ representative pictures of mice with CaMK4$^{+/+}$ BMDMs or CaMK4$^{-/-}$ BMDMs in vivo.
Figures 40A, 40B, 40C:
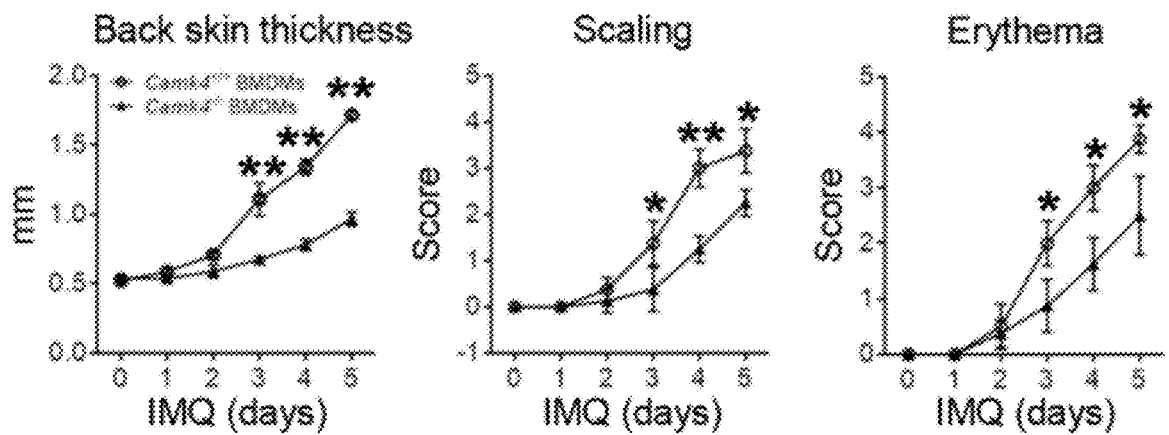
FIG. 40a shows scoring curves of back skin thickness of mice injected of 1×10$^6$ representative pictures of mice with CaMK4$^{+/+}$ BMDMs or CaMK4$^{-/-}$ BMDMs in vivo.
FIG. 40b shows scoring curves of scaling of mice injected of 1×10⁶ representative pictures of mice with CaMK4$^{+/+}$ BMDMs or CaMK4$^{-/-}$ BMDMs in vivo.
FIG. 40c shows scoring curves of erythema of mice injected of 1×10⁶ representative pictures of mice with CaMK4$^{+/+}$ BMDMs or CaMK4$^{-/-}$ BMDMs in vivo.
Figure 41:
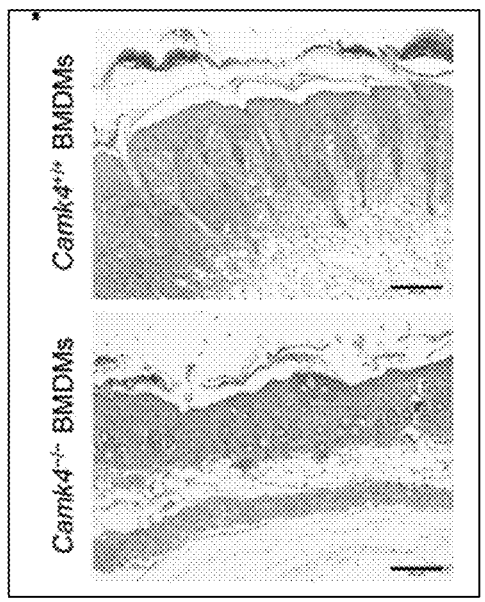
FIG. 41 shows H&E staining of skin sections of mice injected of 1×10⁶ representative pictures of mice with CaMK4$^{+/+}$ BMDMs or CaMK4$^{-/-}$ BMDMs in vivo (scale bar: 200 μm).
Figure 42:
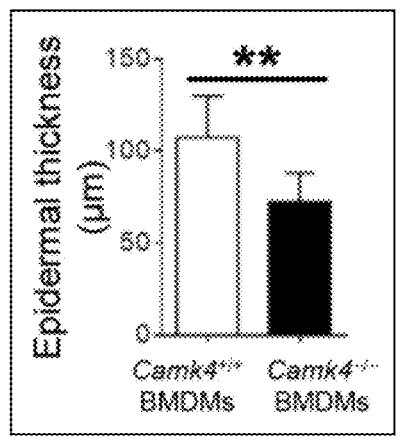
FIG. 42 shows a result of statistical analysis of epidermal thickness mice injected of 1×10⁶ representative pictures of mice with CaMK4$^{+/+}$ BMDMs or CaMK4$^{-/-}$ BMDMs in vivo.
Figure 43:
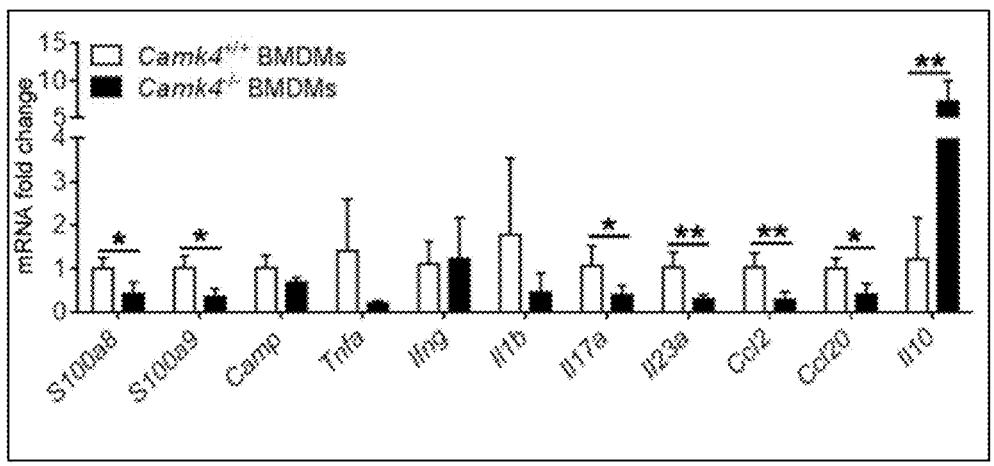
FIG. 43 shows mRNA levels detected by quantitative PCR of skin pathogenic factors induced by IMQ; where data represent twice independent experiments with 5-6 mice in each group, expressed as mean±standard deviation, *p<0.05, **p<0.01.

Referring to FIGS. 33-43, in vivo exogenous supplementation of IL-10 attenuated the psoriasiform phenotype in mice compared to control mice, including reduced skin thickness, scaling, erythema, epidermal thickness and proinflammatory cytokines. The psoriasiform phenotype was attenuated in mice with Camk4-/-BMDM adoptive transfer compared to control mice, including reduced skin thickness, scaling, erythema, epidermal thickness, and proinflammatory cytokines. It's indicated that lack of CaMK4 could restore IL-10 production in macrophages, and IL-10 could reduce IMQ-induced psoriasiform inflammation in mice.

EXAMPLE 7

Detection of Psoriasiform Phenotype and Myeloid Cells in Skin of CaMK4 Lyz2-Cre Mice The construction method of a mouse psoriasis model was the same as that in the example 1.

1) The back skin thickness, scaling and erythema development of mice were observed on days 0 -5 after applying IMQ to the shaved back skin of mice, and scored. The method is the same as that in the example 2.

2) Statistical analysis of epidermal thickness was performed; the method is the same as that in the example 2.

3) The mRNA levels of skin pathogenic factors induced by IMQ were detected by quantitative PCR, and the method was the same as that in the example 1.

4) The proportion and number of F4/80$^+$ CD11c$^+$ cells, CD11b$^+$ DCs and MHC II$^+$ macrophages in mouse skin were detected by flow cytometry. The method was the same as that in the example 3.

Figure 44:
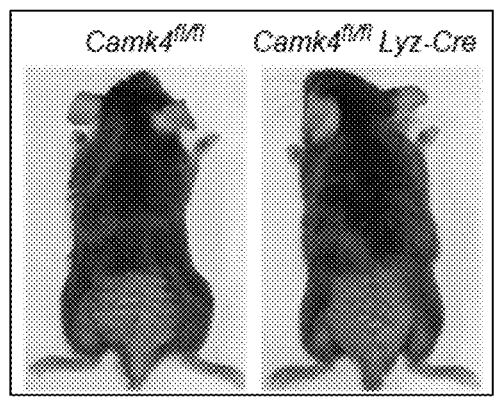
FIG. 44 is a representative picture showing back skin of IMQ induced CaMK4$^{fl/fl}$ mice and CaMK4$^{fl/fl}$ Lyz2-Cre mice.
Figures 45A, 45B, 45C:
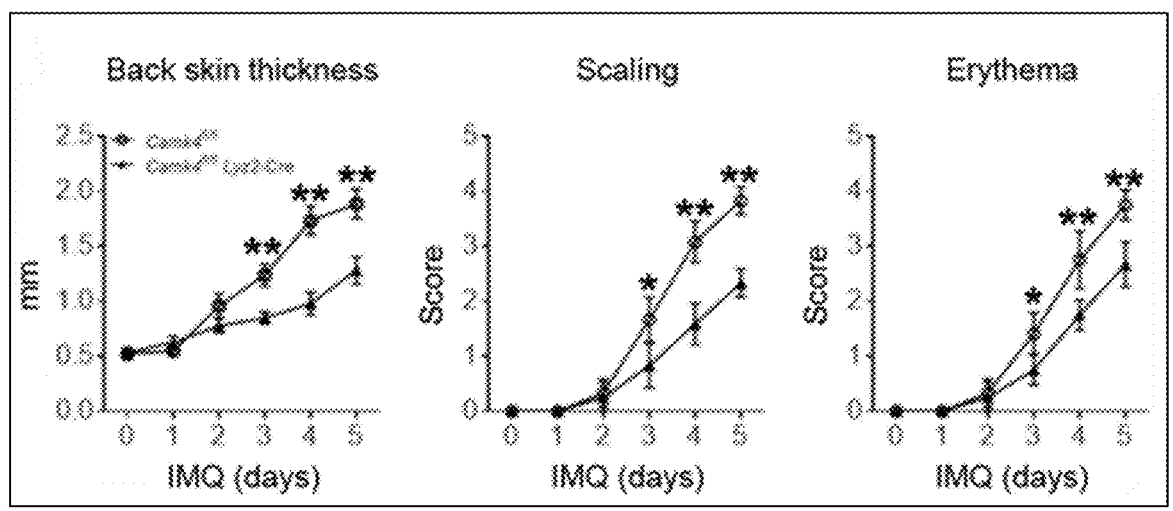
FIG. 45a show scoring curves of back skin thickness of IMQ induced CaMK4$^{fl/fl}$ mice and CaMK4$^{fl/fl}$ Lyz2 Cre mice.
FIG. 45b show scoring curves of scaling of IMQ induced CaMK4$^{fl/fl}$ mice and CaMK4$^{fl/fl}$ Lyz2 Cre mice.
FIG. 45c show scoring curves of erythema of IMQ induced CaMK4$^{fl/fl}$ mice and CaMK4$^{fl/fl}$ Lyz2 Cre mice.
Figure 46:
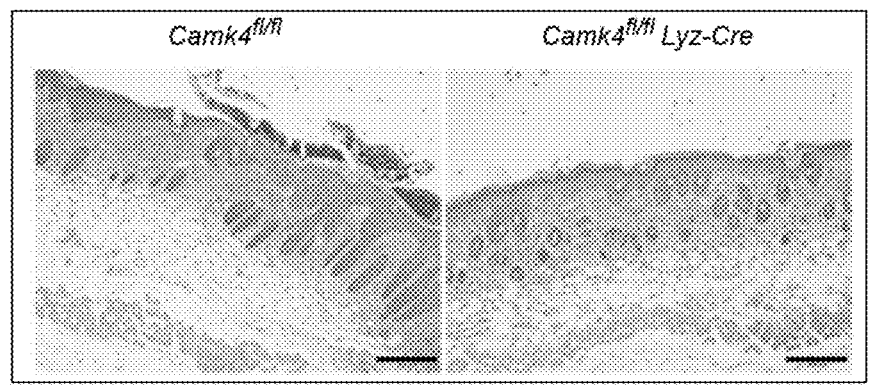
FIG. 46 shows H&E staining of skin sections of IMQ induced CaMK4$^{fl/fl}$ mice and CaMK4$^{fl/fl}$ Lyz2 Cre mice (scale bar: 200 μm).
Figure 47:
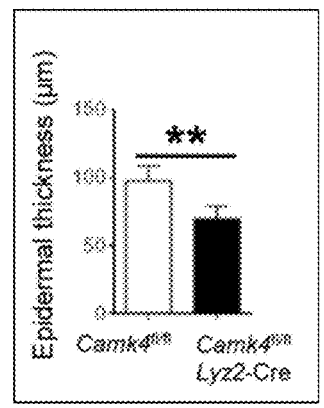
FIG. 47 shows a result of statistical analysis of epidermal thickness of IMQ induced CaMK4$^{fl/fl}$ mice and CaMK4$^{fl/fl}$ Lyz2 Cre mice.
Figure 48:
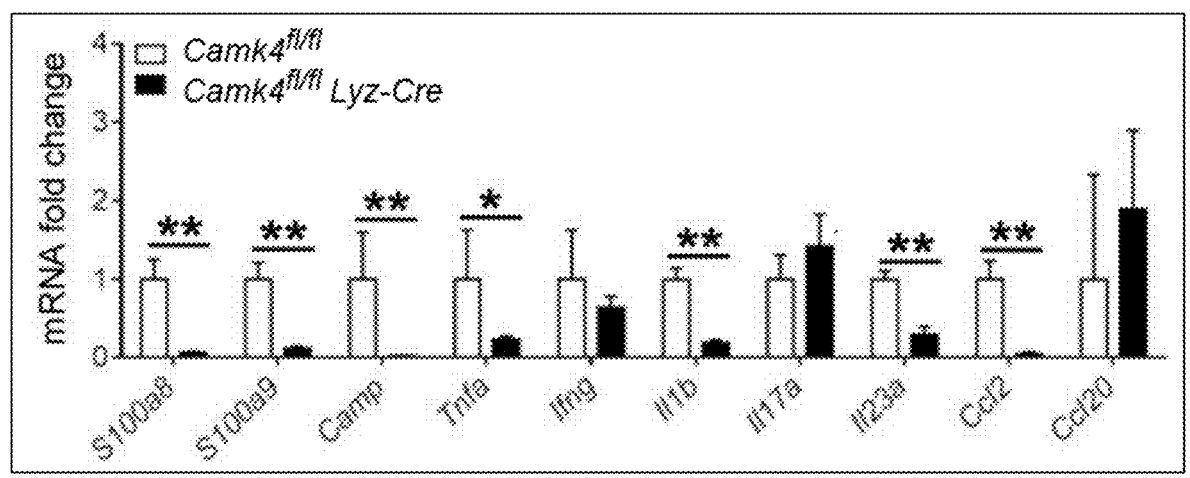
FIG. 48 shows mRNA levels detected by quantitative PCR of skin pathogenic factors of IMQ induced CaMK4$^{fl/fl}$ mice and CaMK4$^{fl/fl}$ Lyz2 Cre mice.
Figure 49:
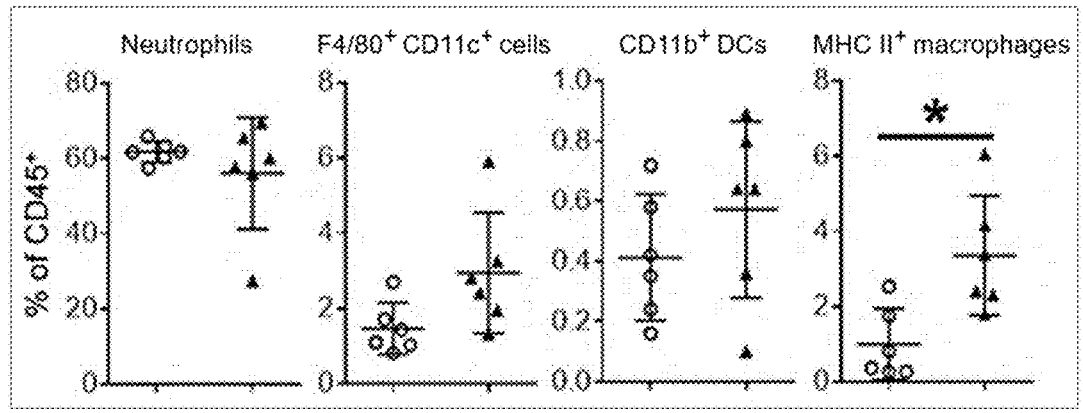
FIG. 49 shows a result of statistical analysis of proportion of neutrophils, F4/80$^+$ CD11c$^+$ cells, CD11b$^+$ DCS and MHC II$^+$ macrophages in mouse skin of IMQ induced CaMK4$^{fl/fl}$ mice and CaMK4$^{fl/fl}$ Lyz2 Cre mice; where data represent twice independent experiments with 6 mice in each group, expressed as mean±standard deviation, *p<0.05, **p<0.01.
Figure 50:
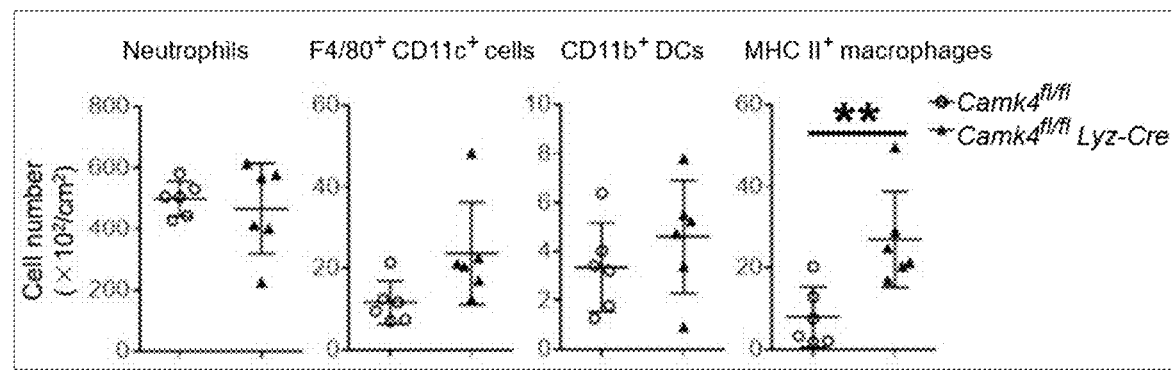
FIG. 50 shows a result of statistical analysis of number of neutrophils, F4/80$^+$ CD11c$^+$ cells, CD11b$^+$ DCS and MHC II$^+$ macrophages in mouse skin of IMQ induced CaMK4$^{fl/fl}$ mice and CaMK4$^{fl/fl}$ Lyz2 Cre mice; where data represent twice independent experiments with 6 mice in each group, expressed as mean±standard deviation, *p<0.05, **p<0.01.

Referring to FIGS. 44-50, the psoriasiform phenotype of Camk4$^{fl/fl}$ Lyz2-Cre mice was less than that of control mice, reduced skin thickness, scaling, erythema, epidermal thickness, and proinflammatory cytokines. Moreover, MHC II$^+$ macrophages were increased in the skin.

EXAMPLE 8

Application of TNF-α and IL-17A Stimulated HaCaT Cells to Simulate the Detection of Psoriasis Cell Model HaCaT cells were transfected with siCaMK4 or control for 24 hours and stimulated with TNF-α (50 ng/ml) and IL-17A (50 ng/ml) for 24 h. The proportion of early and late apoptosis and the proportion of HaCaT cells in G0/G1 phase, S phase and M phase of cell cycle were detected by flow cytometry.

1) The expression of proinflammatory genes was detected by quantitative PCR, and the method was the same as that in example 1;

2) The interaction between CaMK4 and AKT was detected by co-immunocoprecipitation. The prepared cell lysate was incubated with CaMK4 antibody or rabbit IgG at 4° C. overnight; incubated with protein A/G magnetic beads at 4° C. for 1 h. The magnetic beads were rinsed three times, suspended in SDS-PAGE sample buffer, incubated at room temperature for 10 minutes to remove the magnetic beads, and the supernatant was collected and analyzed by Western blot with AKT antibody.

3) The protein levels of different cytokines were detected by Western blot, and the method was the same as that in the example 5.

Figure 51:
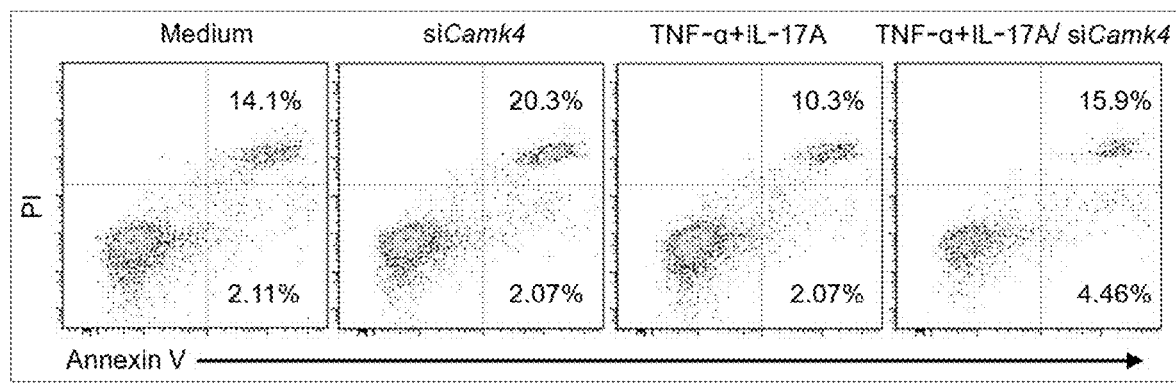
FIG. 51 shows proportion of HaCaT cells with early and late apoptosis detected by flow cytometry after application of TNF-α and IL-17A stimulation to HaCaT cells.
Figure 52:
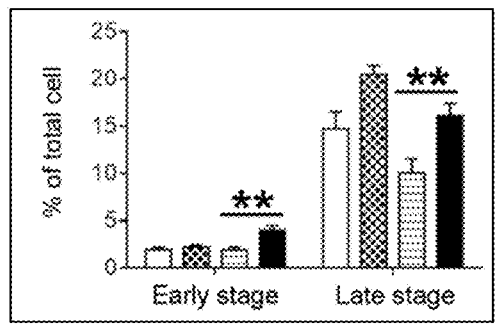
FIG. 52 shows proportion of HaCaT cells with early and late apoptosis detected by flow cytometry after application of TNF-α and IL-17A stimulation to HaCaT cells.
Figure 53:
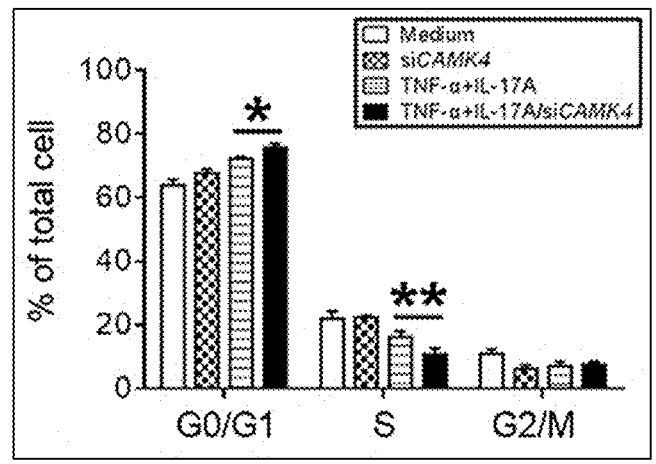
FIG. 53 shows proportion of HaCaT cells in G0/G1 phase, S phase and M phase of cell cycle detected by flow cytometry after application of TNF-α and IL-17A stimulation to HaCaT cells.
Figure 54:
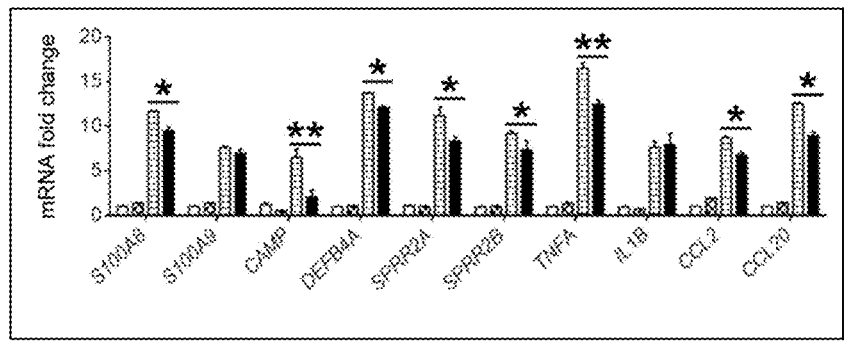
FIG. 54 shows expression of proinflammatory genes detected by quantitative PCR after application of TNF-α and IL-17A stimulation to HaCaT cells.
Figure 55:
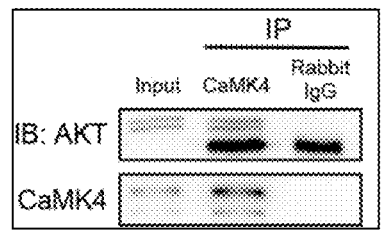
FIG. 55 shows interaction between CaMK4 and AKT detected by co-immunocoprecipitation after application of TNF-α and IL-17A stimulation to HaCaT cells.
Figure 56:
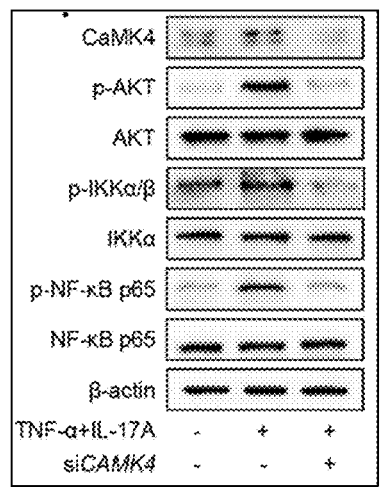
FIG. 56 shows protein levels of CaMK4, p-AKT, AKT, p-IKK α/β, IKK α, p-NK-κB p65 and NF-κ of B p65 detected by Western blot after application of TNF-α and IL-17A stimulation to HaCaT cells; where data represent three times independent experiments, expressed as mean±standard deviation, *p<0.05, **p<0.01.

Referring to FIGS. 51-56, inhibition of CaMK4 in KCs elevated TNF-α and IL-17A stimulated apoptosis of HaCaT cells, decreased cell proliferation and proinflammatory gene expression. CaMK4 affects the downstream NF-κB pathway by interacting with AKT; and indicating that CaMK4 inhibited KCs apoptosis and promoted KCs proliferation and proinflammatory gene expression through the AKT-NF-κB pathway.

EXAMPLE 9

Evaluation of Therapeutic Effect by CaMK4 Inhibitor KN-93 in Mice 62.5 mg of IMQ were applied to the shaved back skin of wild-type mice for 5 days. KN-93 (0.24 mg per mouse) or PBS was injected into mice through tail vein one hour before IMQ application on day 0 and day 2. Samples were collected on day 5 for subsequent experiments.

Figure 57:
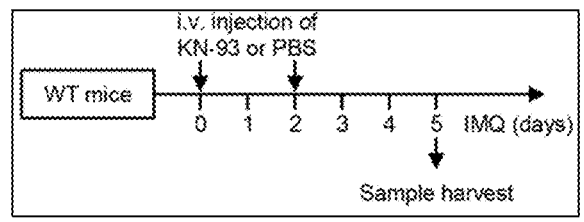
FIG. 57 is a schematic diagram of therapeutic model of mice injected CaMK4 inhibitor KN-93 or PBS in vivo.
Figure 58:
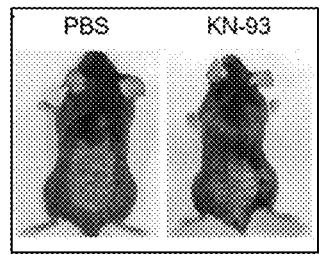
FIG. 58 shows a representative picture showing back skin mice injected CaMK4 inhibitor KN-93 or PBS in vivo.
Figures 59A, 59B, 59C:
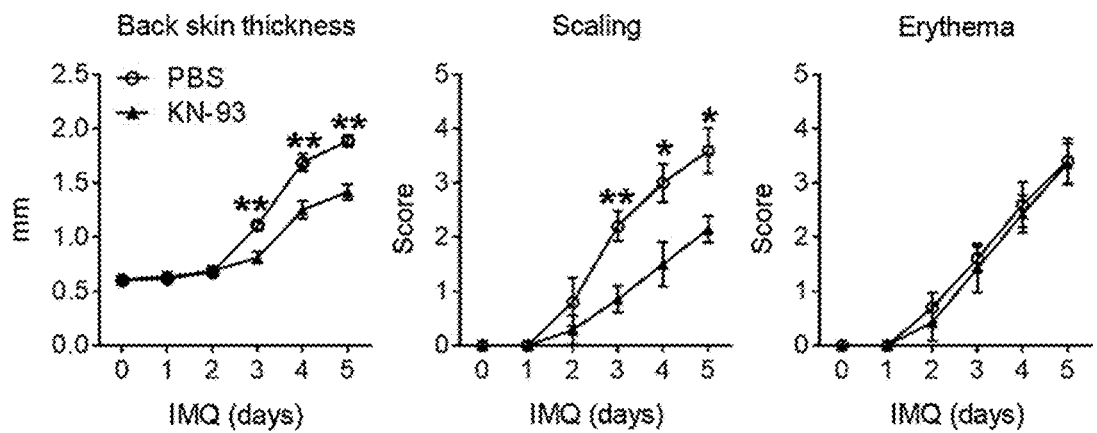
FIG. 59a shows scoring curves of back skin thickness mice injected CaMK4 inhibitor KN-93 or PBS in vivo.
FIG. 59b shows scoring curves of scaling of mice injected CaMK4 inhibitor KN-93 or PBS in vivo.
FIG. 59c shows scoring curves of erythema of mice injected CaMK4 inhibitor KN-93 or PBS in vivo.
Figure 60:
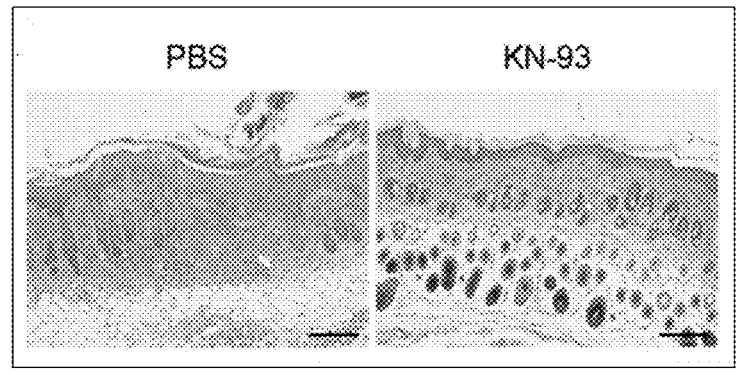
FIG. 60 shows H&E staining of skin sections of mice injected CaMK4 inhibitor KN-93 or PBS in vivo (scale bar: 200 nm).
Figure 61:
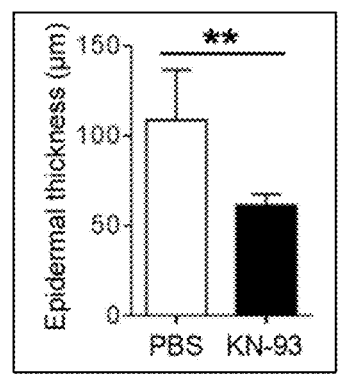
FIG. 61 shows a result of statistical analysis of epidermal thickness of mice injected CaMK4 inhibitor KN-93 or PBS in vivo.
Figure 62:
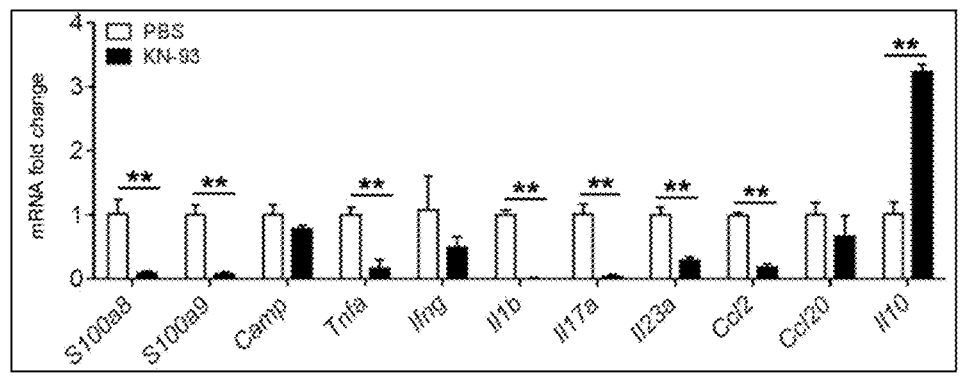
FIG. 62 shows mRNA levels detected by quantitative PCR of skin pathogenic factors induced by IMQ of mice injected CaMK4 inhibitor KN-93 or PBS in vivo; where data represent twice independent experiments with 5-7 mice in each group, expressed as mean±standard deviation, *p<0.05, **p<0.01.

Referring to FIGS. 57-62, the psoriasiform phenotype of KN-93 treated mice was less than that of control mice, including reduced skin thickness, scaling, epidermal thickness and proinflammatory cytokines. Moreover, the mRNA level of IL-10 in skin of KN-93 treated mice was higher than that of control mice.

The above examples only describe preferred modes of the invention and do not limit the scope of the invention. Without departing from the design spirit of the invention, various modifications and changes made by those skilled in the art to the technical solutions of the invention shall fall within the protection scope determined by the claims of the invention.

What is claimed is:

1. An application method of a calcium/calmodulin-dependent protein kinase IV (CaMK4) inhibitor, comprising:
   administering the CaMK4 inhibitor to patients with psoriasis at a target dose to prevent and treat psoriasis by taking CaMK4 as a medicine target;
   wherein the CaMK4 inhibitor is KN-93 with the target dose of 10 micromoles per liter (μM); and
   wherein the CaMK4 inhibitor is used to block a recovery of interleukin-10 (IL-10) caused by the CaMK4.

2. The application method according to claim 1, wherein the CaMK4 inhibitor takes the CaMK4 as the medicine target at genetic level and/or protein level.

3. The application method according to claim 1, wherein the CaMK4 inhibitor is used to hinder a protein expression of the CaMK4 or a messenger ribonucleic acid (mRNA) expression of the CaMK4.

* * * * *